United States Patent
Srinivasan et al.

(10) Patent No.: US 11,207,470 B2
(45) Date of Patent: Dec. 28, 2021

(54) PEN NEEDLE EXCHANGE SYSTEM

(71) Applicant: Becton, Dickinson and Company, Franklin Lakes, NJ (US)

(72) Inventors: Sudarsan Srinivasan, North Brunswick, NJ (US); Cole Constantineau, Cambridge, MA (US); Michel Bruehwiler, Newton, MA (US); Tyson Montidoro, Davie, FL (US); Jeffrey Chagnon, Somerville, MA (US); Mohammadreza Ramezanifard, San Diego, CA (US); Stefan Gisler, Winterthur (CH)

(73) Assignee: Becton, Dickinson and Company, Franklin Lakes, NJ (US)

( * ) Notice: Subject to any disclaimer, the term of this patent is extended or adjusted under 35 U.S.C. 154(b) by 342 days.

(21) Appl. No.: 16/095,172

(22) PCT Filed: Mar. 31, 2017

(86) PCT No.: PCT/US2017/025325
§ 371 (c)(1),
(2) Date: Oct. 19, 2018

(87) PCT Pub. No.: WO2017/189168
PCT Pub. Date: Nov. 2, 2017

(65) Prior Publication Data
US 2019/0143051 A1 May 16, 2019

Related U.S. Application Data

(60) Provisional application No. 62/328,670, filed on Apr. 28, 2016.

(51) Int. Cl.
*A61M 5/32* (2006.01)
*A61M 5/00* (2006.01)
(Continued)

(52) U.S. Cl.
CPC ............ *A61M 5/3293* (2013.01); *A61M 5/32* (2013.01); *A61M 5/3202* (2013.01);
(Continued)

(58) Field of Classification Search
CPC ............ A61M 5/3157; A61M 5/31568; A61M 2005/3126; A61M 2205/3331;
(Continued)

(56) References Cited

U.S. PATENT DOCUMENTS 5,829,589 A 11/1998 Nguyen et al.
5,873,462 A 2/1999 Nguyen et al.
(Continued)

FOREIGN PATENT DOCUMENTS

EP 2119423 A1 11/2009
EP 2420270 A2 2/2012
(Continued)

OTHER PUBLICATIONS

Li-Yuan Chang et al., "Integrated Flow Sensing for Focal Biochemical Stimulation", Proceedings of the Third IEEE International Conference on Nano/Micro Engineered and Molecular Systems, Jan. 6-9, 2008, Sanya, China, pp. 921-926, (6 Pages Total).

*Primary Examiner* — Bhisma Mehta
*Assistant Examiner* — John J Crawford
(74) *Attorney, Agent, or Firm* — Dickinson Wright PLLC

(57) ABSTRACT

An electronic system (200) connectable to a medication delivery pen (4) and a needle assembly (2, 102), the electronic system (200) exchanging data regarding a medicament traveling from the medication delivery pen (4) to the needle assembly (2, 102), the electronic system (200) comprising a hub (202) having a spike (204) that is configured to engage the medication delivery pen (4) and pierce a reservoir septum of the medication delivery pen (4), a flow sensor (220) that is in fluid communication with the hub
(Continued)

(202) to measure flow data of the medicament, a circuit board (250) electrically contacting the flow sensor (220) to process and transmit the flow data, the circuit board (250) including a fluid path hole (254) to route a flow of medicament, and a septum body (270, 284) that is configured to provide fluid communication between the flow sensor (220) and one of a plurality of needles (40, 124) of the needle assembly (2, 102) to administer the medicament to a patient.

23 Claims, 23 Drawing Sheets

(51) Int. Cl.
 *A61M 5/24* (2006.01)
 *A61M 5/34* (2006.01)
 *G16H 20/17* (2018.01)

(52) U.S. Cl.
 CPC ..... *A61M 5/3298* (2013.01); *A61M 2005/004* (2013.01); *A61M 2005/2474* (2013.01); *A61M 2005/342* (2013.01); *A61M 2205/3331* (2013.01); *A61M 2205/3334* (2013.01); *A61M 2205/3561* (2013.01); *A61M 2205/3592* (2013.01); *A61M 2205/52* (2013.01); *G16H 20/17* (2018.01)

(58) Field of Classification Search
 CPC .. A61M 2205/3334; A61M 2205/3561; A61M 2205/3576; A61M 2205/3592; A61M 5/32; A61M 5/3202; A61M 5/3295; A61M 2005/004; A61M 5/178; A61M 5/20; A61M 5/24; A61M 5/28; G16H 20/17; G06F 19/30; G06F 19/32; G06F 19/34; G06F 19/3468; G06Q 50/22; G06Q 50/24
 See application file for complete search history.

(56) References Cited

U.S. PATENT DOCUMENTS

| | | | |
|---|---|---|---|
| 5,931,817 | A | 8/1999 | Nguyen et al. |
| 6,277,099 | B1* | 8/2001 | Strowe .............. A61M 5/31553 604/186 |
| 8,876,780 | B2 | 11/2014 | Bruehwiler et al. |
| 9,101,724 | B2 | 8/2015 | Chapin et al. |
| 9,107,988 | B2 | 8/2015 | Bruehwiler et al. |
| 9,155,838 | B2 | 10/2015 | Bilton et al. |
| 9,381,303 | B2 | 7/2016 | Abhijitsinh et al. |
| 9,717,860 | B2 | 8/2017 | Bruehwiler et al. |
| 10,029,042 | B2 | 7/2018 | Searle et al. |
| 2001/0014792 | A1 | 8/2001 | West et al. |
| 2002/0020646 | A1 | 2/2002 | Groth et al. |
| 2002/0020647 | A1 | 2/2002 | Groth |
| 2003/0163089 | A1* | 8/2003 | Bynum .............. A61M 5/14566 604/154 |
| 2004/0210199 | A1* | 10/2004 | Atterbury ................ G01D 5/25 604/224 |
| 2005/0084631 | A1 | 4/2005 | Anderson |
| 2008/0312604 | A1 | 12/2008 | Boesen |
| 2010/0217206 | A1 | 8/2010 | Lum et al. |
| 2011/0068034 | A1 | 3/2011 | Hwang et al. |
| 2011/0185821 | A1* | 8/2011 | Genosar ................ G01F 1/7046 73/861.08 |
| 2011/0313395 | A1* | 12/2011 | Krulevitch ............ A61M 5/315 604/504 |
| 2012/0004620 | A1 | 1/2012 | Spool et al. |
| 2012/0016315 | A1 | 1/2012 | Radmer et al. |
| 2012/0041373 | A1* | 2/2012 | Bruehwiler ......... A61M 5/3243 604/173 |
| 2012/0041381 | A1 | 2/2012 | Raj et al. |
| 2012/0041383 | A1 | 2/2012 | Bruehwiler et al. |
| 2012/0041390 | A1 | 2/2012 | Spool et al. |
| 2013/0041321 | A1* | 2/2013 | Cross .................. A61M 5/2448 604/189 |
| 2013/0053751 | A1 | 2/2013 | Holtham |
| 2014/0076758 | A1 | 3/2014 | Dasbach et al. |
| 2014/0123479 | A1 | 5/2014 | Dasbach |
| 2014/0262884 | A1 | 9/2014 | Priebe et al. |
| 2014/0299622 | A1 | 10/2014 | Hofmann et al. |
| 2014/0339113 | A1 | 11/2014 | Hofmann et al. |
| 2015/0025469 | A1 | 1/2015 | Larsen et al. |
| 2015/0163898 | A1 | 6/2015 | Mokhtarzad |
| 2015/0273161 | A1* | 10/2015 | Bengtsson ............ A61M 5/001 604/198 |
| 2015/0335827 | A1 | 11/2015 | Stefansen et al. |
| 2015/0346184 | A1* | 12/2015 | Galasso ............ A61B 5/14532 204/403.01 |
| 2016/0000992 | A1* | 1/2016 | Steel ...................... A61M 5/002 604/198 |
| 2016/0030683 | A1* | 2/2016 | Taylor ..................... A61M 5/32 604/151 |
| 2016/0074587 | A1 | 3/2016 | Searle et al. |
| 2016/0082195 | A1 | 3/2016 | Atterbury et al. |
| 2016/0106925 | A1 | 4/2016 | Boesen |
| 2016/0339431 | A1* | 11/2016 | Shmilovich ....... B01L 3/502707 |
| 2016/0378951 | A1* | 12/2016 | Gofman ............ A61M 5/31546 604/504 |
| 2018/0361067 | A1* | 12/2018 | Sall ......................... A61M 5/28 |

FOREIGN PATENT DOCUMENTS

| | | |
|---|---|---|
| EP | 2586475 A1 | 5/2013 |
| EP | 2696913 B1 | 9/2015 |
| WO | 2008/150715 A1 | 12/2008 |
| WO | 2014/020001 A1 | 2/2014 |
| WO | 2016/050902 A1 | 4/2016 |
| WO | WO-2016050902 A1 * | 4/2016 ............... A61M 5/24 |

* cited by examiner

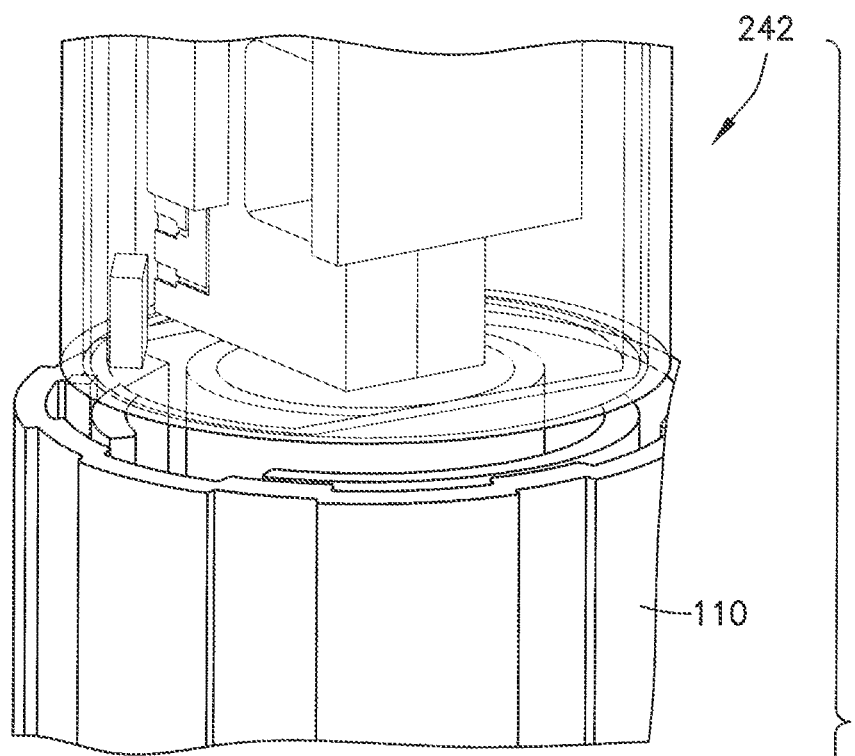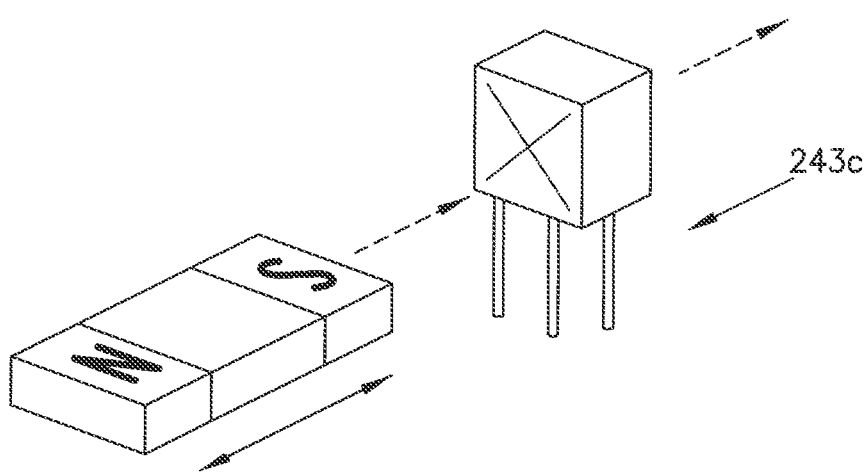
FIG.27

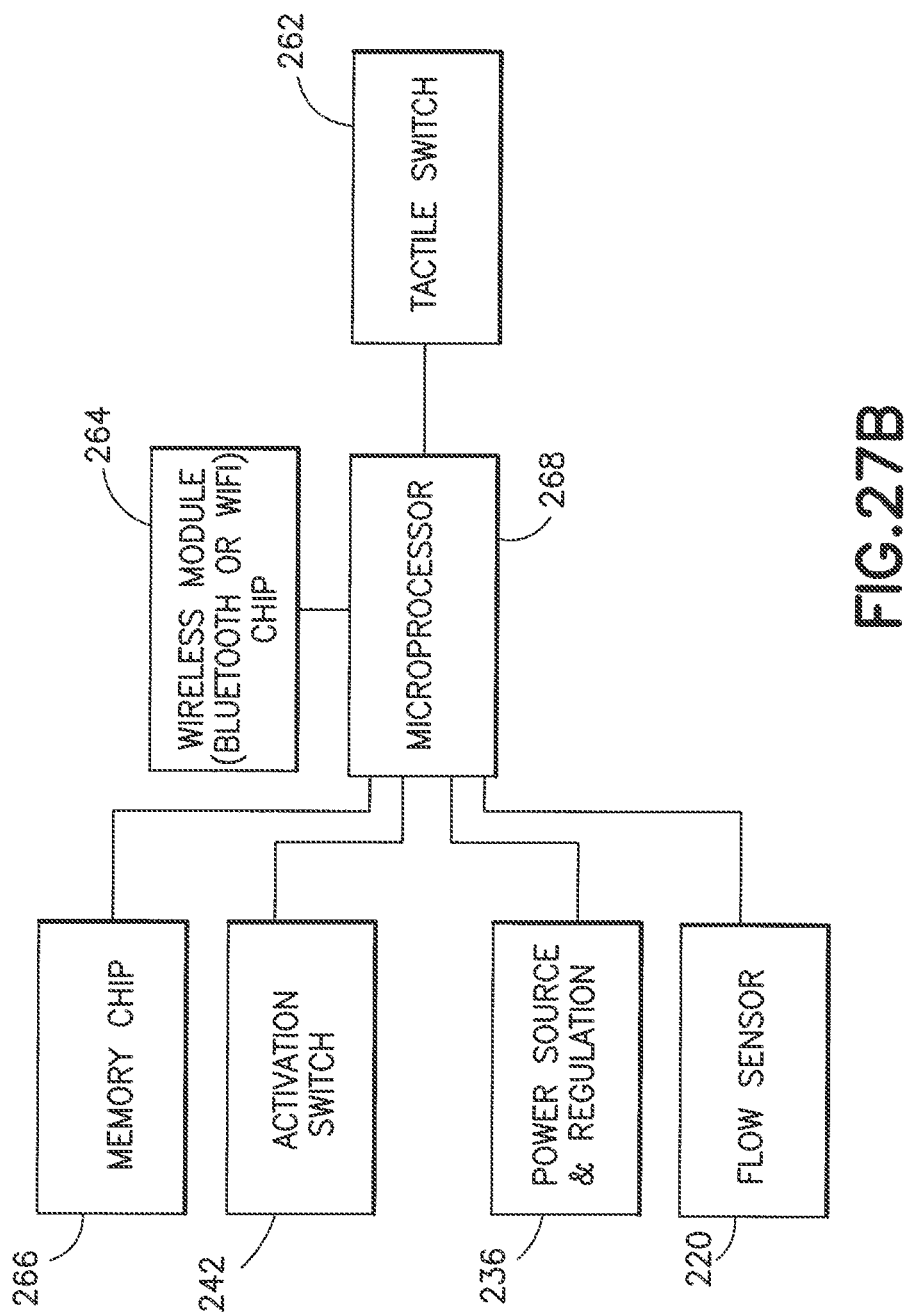

PEN NEEDLE EXCHANGE SYSTEM

This application claims the benefit under 35 U.S.C. § 119(e) of U.S. Provisional Patent Application Ser. 62/328,670, filed on Apr. 28, 2016, which is hereby incorporated by reference in its entirety.

FIELD

Various exemplary embodiments of the invention relate to medication pens.

BACKGROUND

Medication pens are typically used to inject medication into a patient. A person who must periodically self-inject doses of medication will typically carry a medication pen and several single-use pen needles. A medication pen is designed for safety and sterility. However, inefficiencies and inconveniences arise.

SUMMARY OF THE INVENTION

It is an aspect of the present invention to provide an electronic exchange system that is attachable to a medication pen to analyze medicament flow and communicate medicament data. Such an electronic exchange system provides advantages in separating a patient end and a non-patient end by acting as an intermediary between the medication pen and an injection surface. The electronic exchange system also advantageously allows for engagement and disengagement to the medication pen. Moreover, electrical components of the electronic exchange system are advantageously sealed from medicament flow. Specifically, the medicament flow is strategically routed around various electrical components for system compactness, improved reliability and an improved operational interface.

Having a magazine of needles available for medication delivery reduces needle reuse. Needle reuse is undesired for at least the following reasons. The needle dulls after a single use and so subsequent use may cause pain to the patient. Multiple needle use can also reduce the strength of the needle tip which may cause a potential fracture. Also, needle reuse increases sanitary concerns and health risks to the patient.

The needle assembly of the present invention advantageously reduces reuse for at least the following reasons. Although patients may desire to financially benefit from using a needle multiple times, the needle assembly is configured to prevent each of the plurality of needles from being used more than once. Convenience is another reason patients reuse needles. Patients may also be concerned about not having another needle available for use or not having access to supplies. However, the needle assembly conveniently provides multiple needles so that an unused needle is more readily available.

The foregoing and/or other aspects of the present invention can be achieved by providing an electronic system connectable to a medication delivery pen and a needle assembly, the electronic system exchanging data regarding a medicament traveling from the medication delivery pen to the needle assembly, the electronic system comprising a hub having a spike that is configured to engage the medication delivery pen and pierce a reservoir septum of the medication delivery pen, a flow sensor that is in fluid communication with the hub to measure flow data of the medicament, a circuit board electrically contacting the flow sensor to process and transmit the flow data, the circuit board including a fluid path hole to route a flow of medicament, and a septum body that is configured to provide fluid communication between the flow sensor and one of a plurality of needles of the needle assembly to administer the medicament to a patient.

The foregoing and/or other aspects of the present invention can also be achieved by a method of operating an electronic system connectable to a medication delivery pen and a needle assembly, the electronic system exchanging data regarding a medicament traveling from the medication delivery pen to the needle assembly, the method comprising piercing a reservoir septum of the medication delivery pen with a spike enclosed in a hub, connecting the medication delivery pen to the hub, providing fluid communication between the spike and a flow sensor to measure flow data of the medicament, processing and transmitting the flow data from the flow sensor to a circuit board, and routing medicament flow from the flow sensor, through the circuit board and to a septum body for delivery of the medicament to a patient when the septum body is connected to the needle assembly.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which:

FIG. 27 illustrates an electronic exchange system including an activation switch being a hall effect sensor;

FIG. 27B illustrates a block diagram of the operation of the flexible circuit board in the electronic exchange system;

DETAILED DESCRIPTION OF EXEMPLARY EMBODIMENTS

Figure 1B:
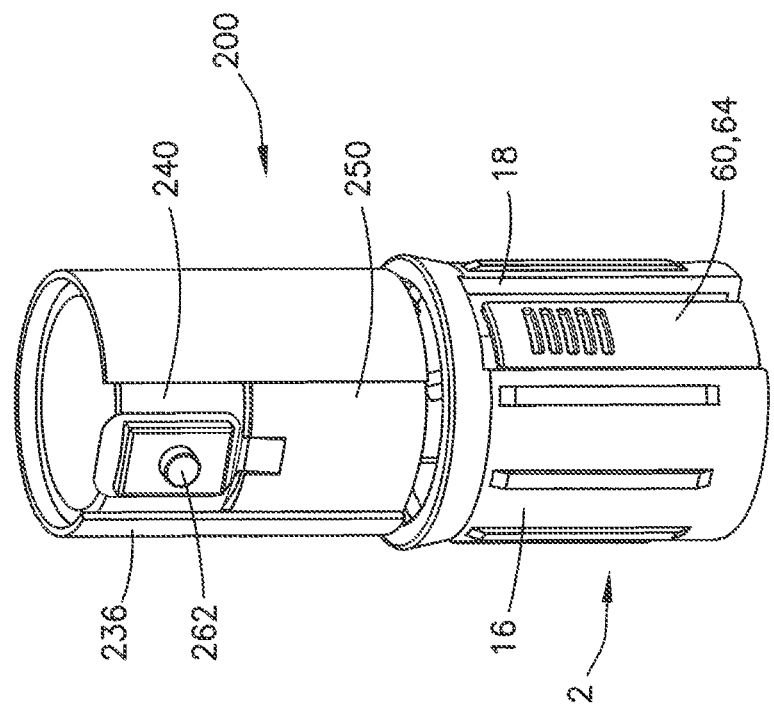
FIG. 1b illustrates the front perspective view of the electronic exchange system attached to the needle assembly of FIG. 1a with a frame or cover removed.
Figure 1A:
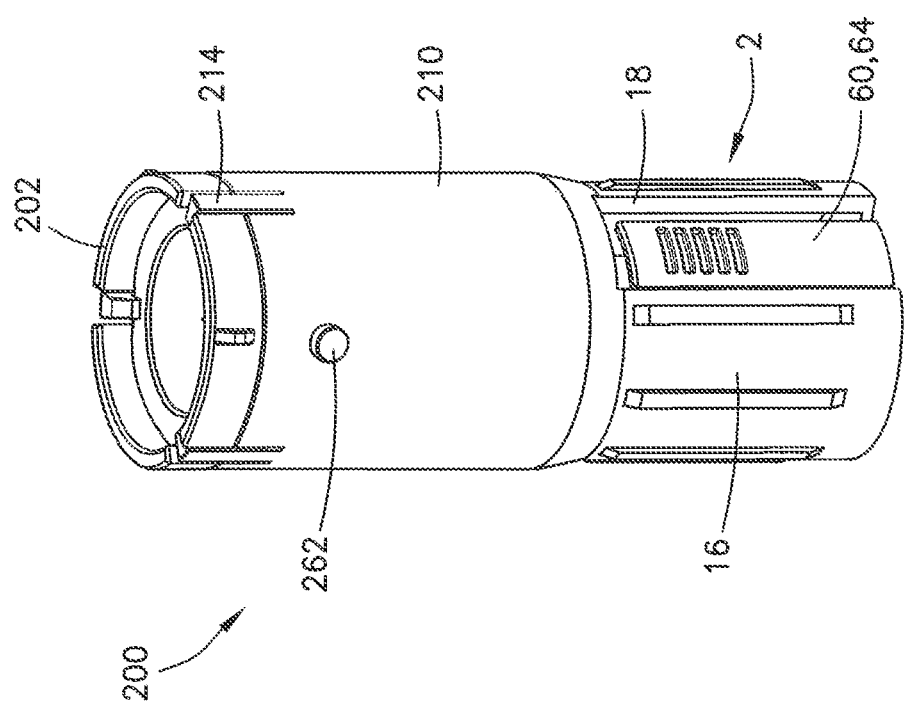
FIG. 1a illustrates a front perspective view of an exemplary electronic exchange system attached to a needle assembly.
Figure 2:
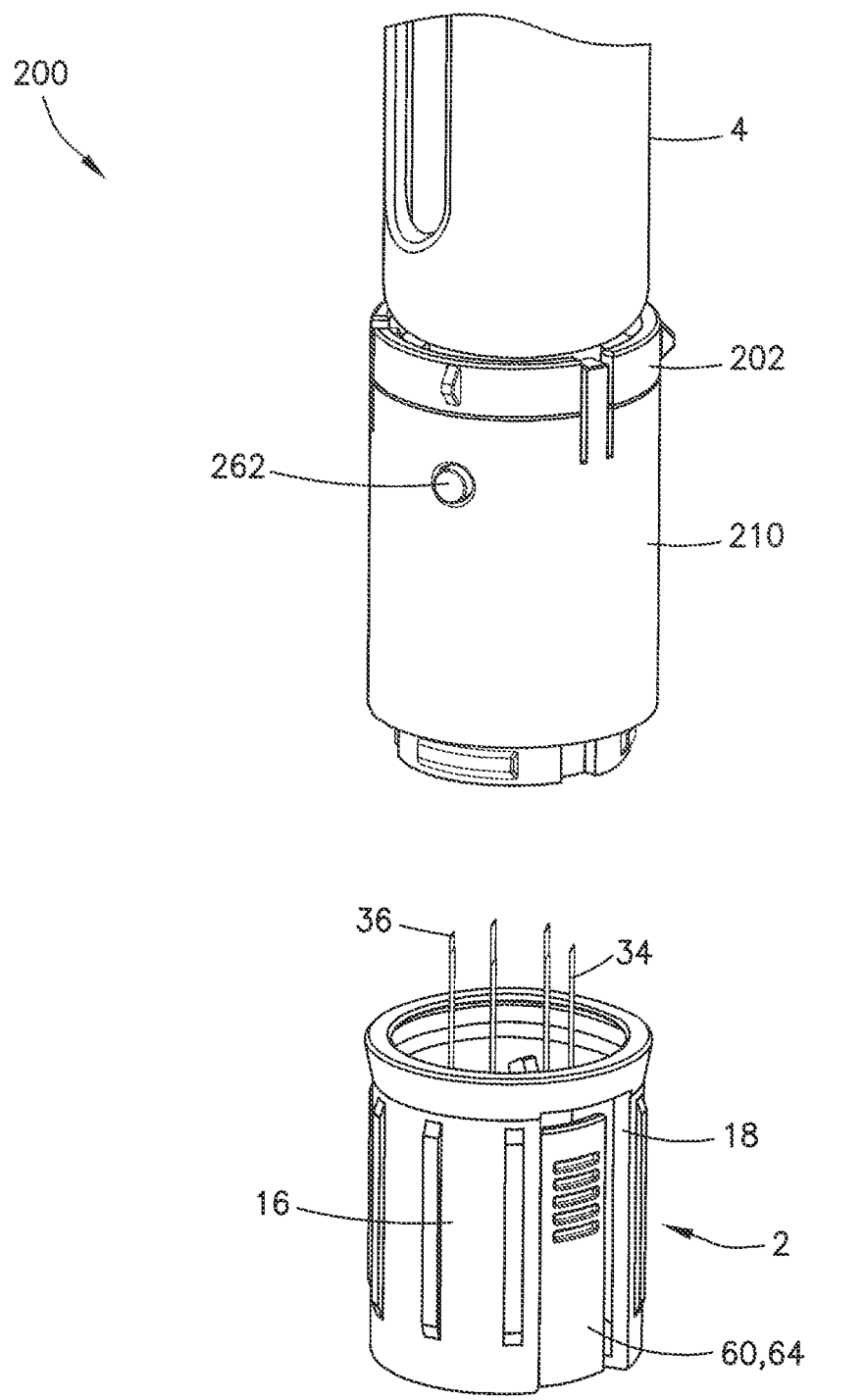
FIG. 2 illustrates a front perspective view of an electronic exchange system, connected to a medication delivery pen and attachable to a needle assembly.

FIGS. 1a, 1b and 2, according to one embodiment, illustrate an exemplary electronic exchange system 200 engaged to a needle assembly 2. The electronic exchange system 200 is enclosed by a frame 210 which is fixed to a hub 202 via a plurality of flanges 214. The electronic exchange system 200 is electrically activated for use by a tactile switch 262. Additional components of the electronic exchange system 200 include a flexible battery 236, a foam pad 240 and a flexible circuit board 250. Further details of each of these features are described below.

The electronic exchange system 200 of FIGS. 1a, 1b and 2 is connected to an exemplary needle assembly 2. The needle assembly 2 includes a selector ring 16 having a selector opening 18 that exposes a peel tab 60 including a tab 64 so that one of a plurality of hollow needles 34 may be exposed for medication delivery. Further details of the needle assembly 2 are described below.

FIG. 2, according to one embodiment, illustrates a typical medication delivery pen 4 used for injecting medicament, such as liquid drugs, into a living body. The electronic exchange system 200 is mounted on the medication delivery pen 4 to analyze medicament flow. The needle assembly 2 is configured to mount on the electronic exchange system 200 to enhance medication delivery by providing the plurality of needles 34 with sharp proximal ends 36 for use. The needle assembly 2 can be replaced so that the medication delivery pen 4 and the electronic exchange system 200 can continue to operate as needed. Benefits and advantages of the electronic exchange system 200 cooperating with the medication delivery pen 4 and the needle assembly 2 are described below.

Figure 3:
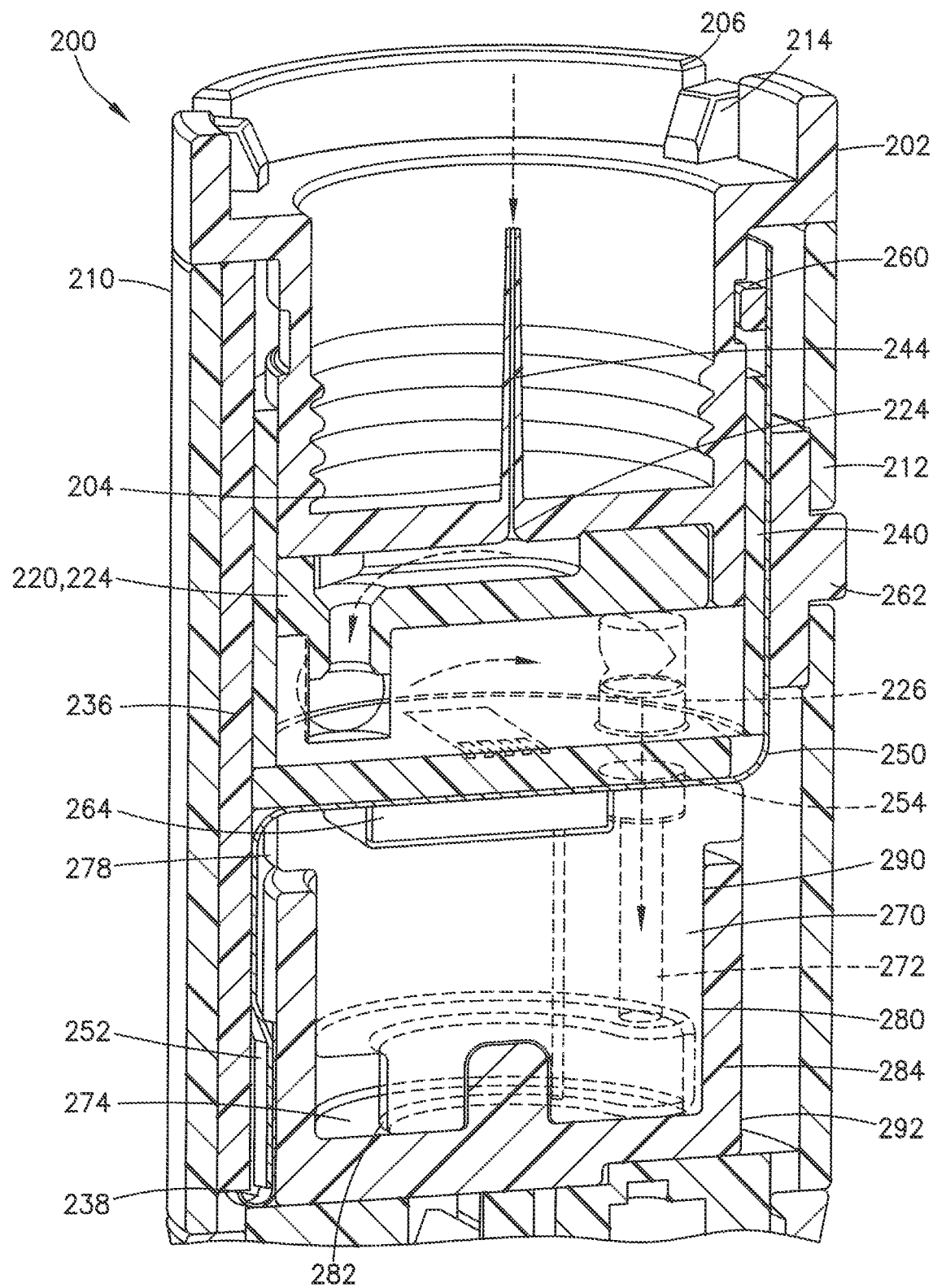
FIG. 3 illustrates a cross sectional view of the electronic exchange system.
Figure 8:
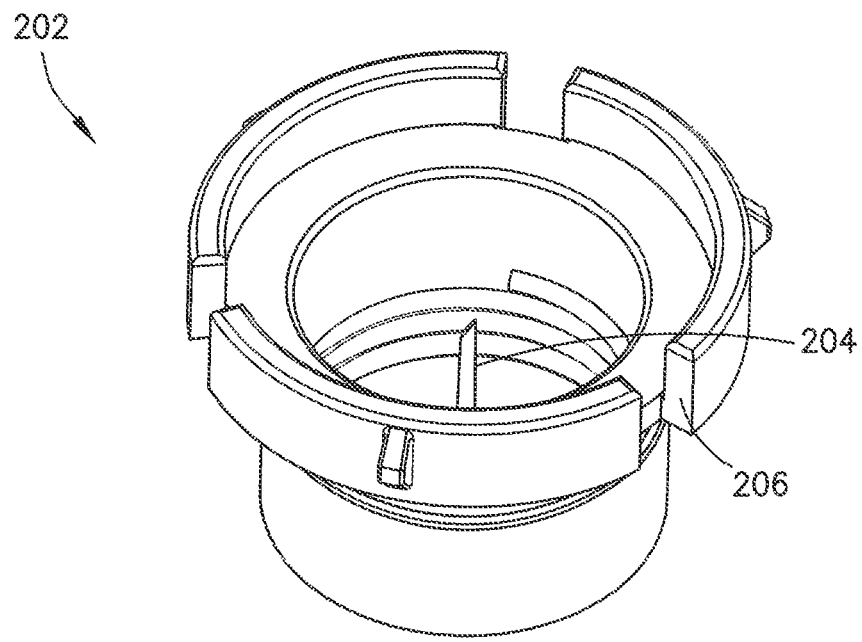
FIG. 8 illustrates a front perspective view of a hub.
Figure 9:
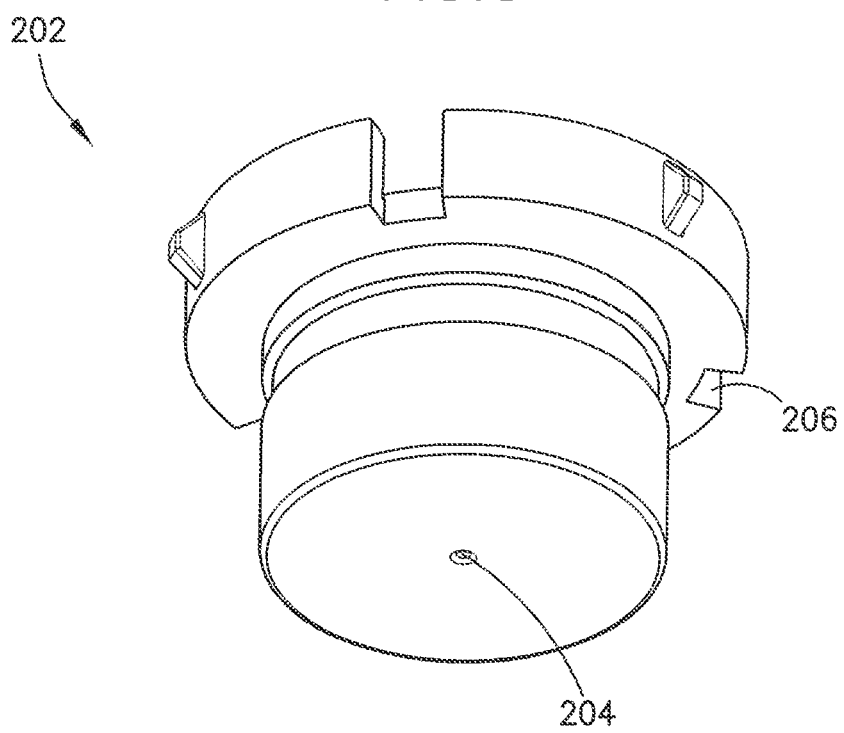
FIG. 9 illustrates a rear perspective view of the hub.

According to one embodiment, FIG. 3 illustrates a cross sectional view of the electronic exchange system 200. The hub 202 includes a hollow spike 204 and a plurality of notches 206. As illustrated in FIGS. 8 and 9, the hollow spike 204 is configured to pierce a vial, cartridge or reservoir septum (not shown) of the medication delivery pen 4. When the electronic exchange system 200 is mounted on the medication delivery pen (non-patient end), a sharpened proximal end of the hollow spike 204 pierces the reservoir septum to establish fluid communication between the electronic exchange system 200 and the medication delivery pen 4. Specifically, the hollow spike 204 piercing the reservoir septum provides fluid communication between the electronic exchange system 200 and an insulin cartridge, for example, of the medication delivery pen 4.

Figure 12:
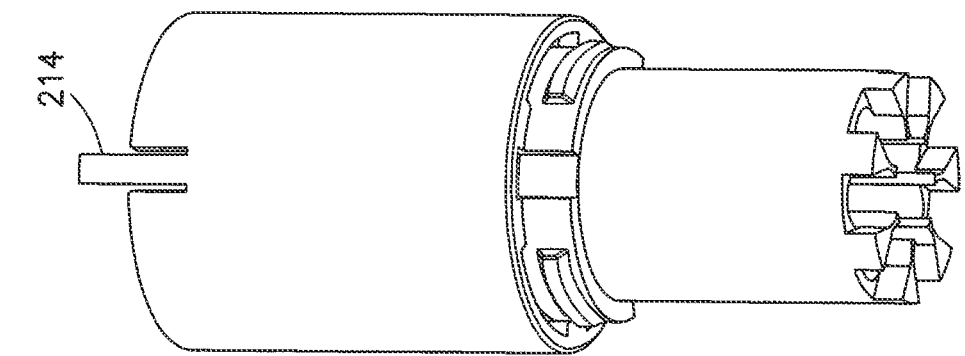
FIG. 12 illustrates a bottom perspective view of the frame.
Figure 11:
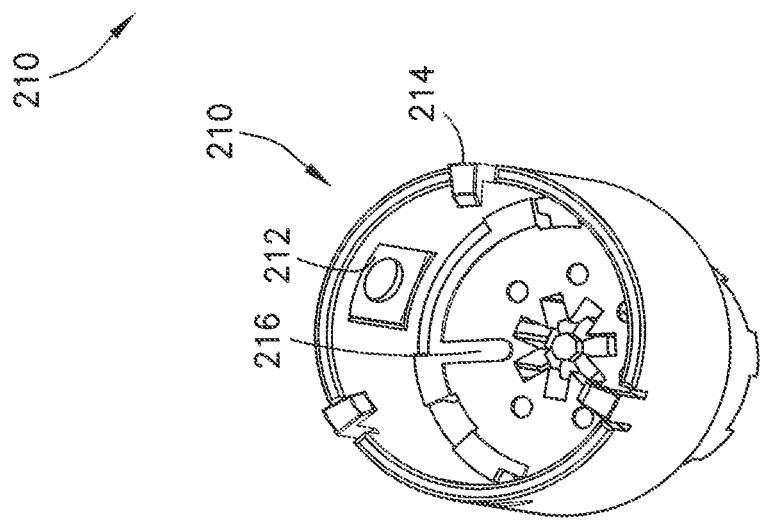
FIG. 11 illustrates a top perspective view of the frame.
Figure 10:
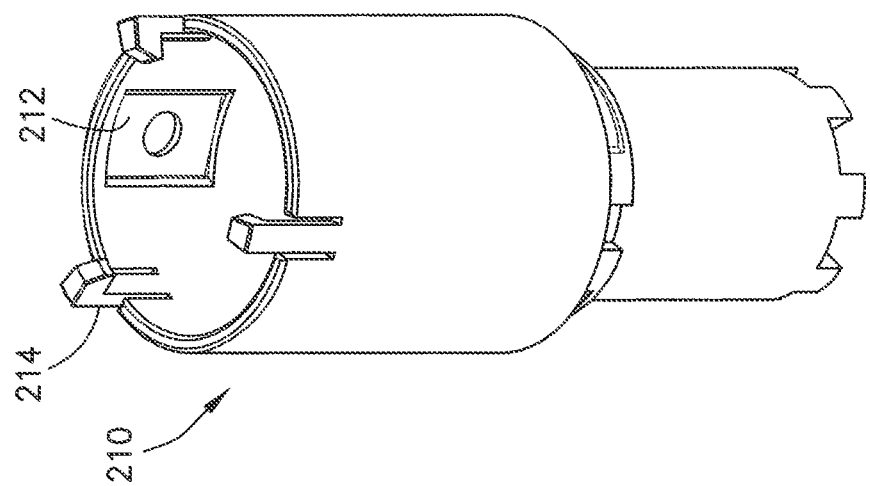
FIG. 10 illustrates a front perspective view of the frame.
Figure 13:
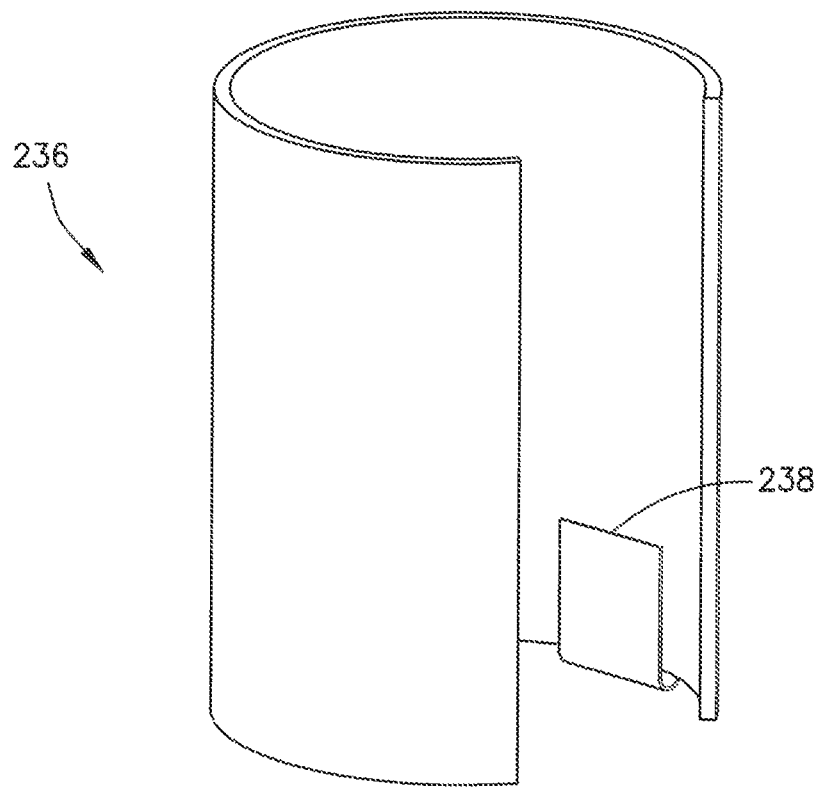
FIG. 13 illustrates a top perspective view of a flexible battery.

The hub 202 also includes a plurality of notches 206 that each engages one of the plurality of flanges 214 in the frame 210. As illustrated in FIG. 1a, the hub 202 and the plurality of notches 206 are externally visible to a user. The plurality of flanges 214, as illustrated in FIGS. 10-12, extends from a top surface of the frame 210. Such a configuration secures the frame 210 to the hub 202. Preferably, the hub 202 is translucent and configured to illuminate from the light emitted from LEDs 260. As described below, such a configuration advantageously indicates device status to the user since the hub 202 is externally visible.

The frame 210, according to one embodiment, further includes a frame pocket 212 including a hole, and a protruding key 216. As illustrated in FIGS. 10-12, the frame pocket 212 is a substantially square shaped recess along an inner diameter of the frame 210. A hole extends through the frame pocket 212 at its center. The frame pocket 212 is configured to carry a substantially square shaped tactile switch 262 although a variety of shapes of the frame pocket 212 and the tactile switch 262 is contemplated. The tactile switch 262 extends through the hole of the frame pocket 212 so that the user can compress the tactile switch 262 and activate the electronic exchange system 200.

The protruding key 216 is located at a bottom inner surface of the frame 210 where the components of the electronic exchange system 200 are disposed. The protruding key 216 extends from the bottom inner surface to engage a corresponding groove, recess or extruded key 288 in a lower septum 284. This engagement provides alignment between the lower septum 284 and the frame 210. Further information regarding the lower septum 284 is described below.

Figure 14:
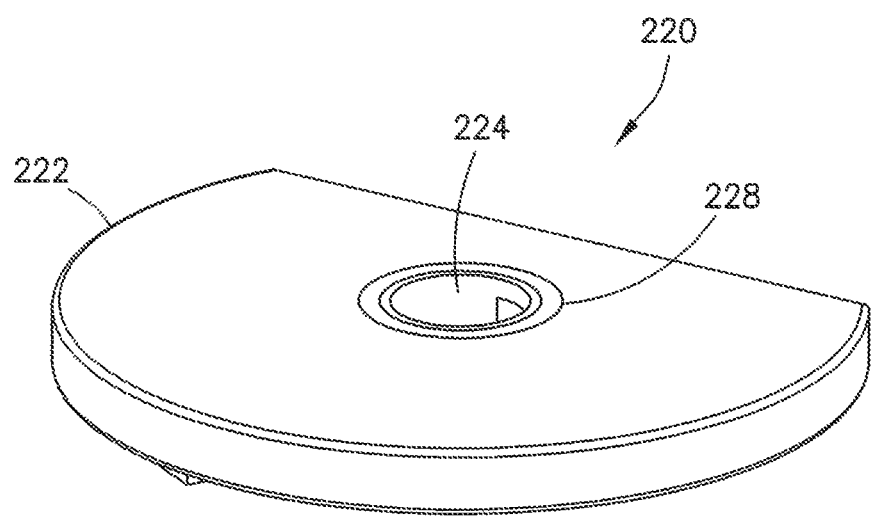
FIG. 14 illustrates a top perspective view of a flow sensor.
Figure 15:
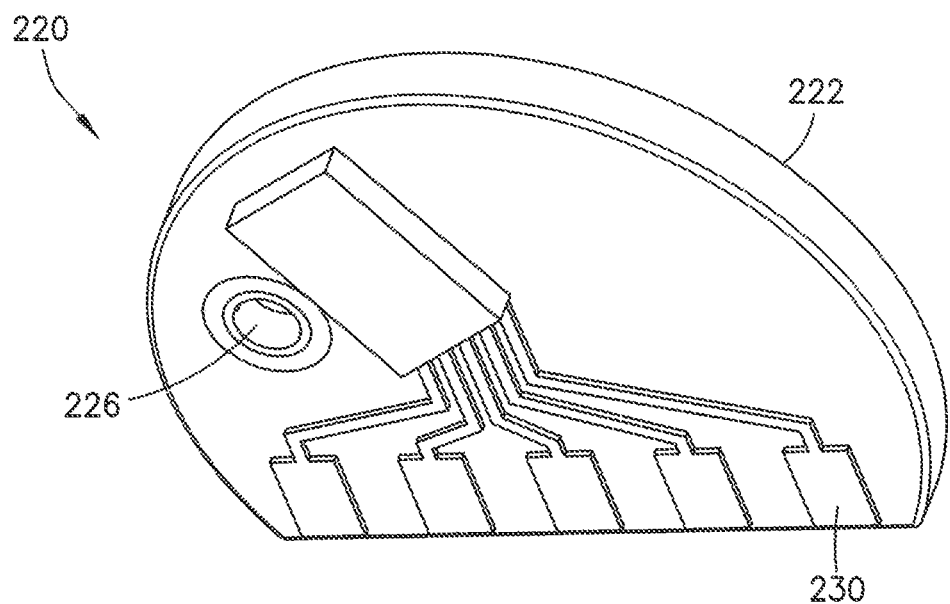
FIG. 15 illustrates a bottom perspective view of the flow sensor.
Figure 16:
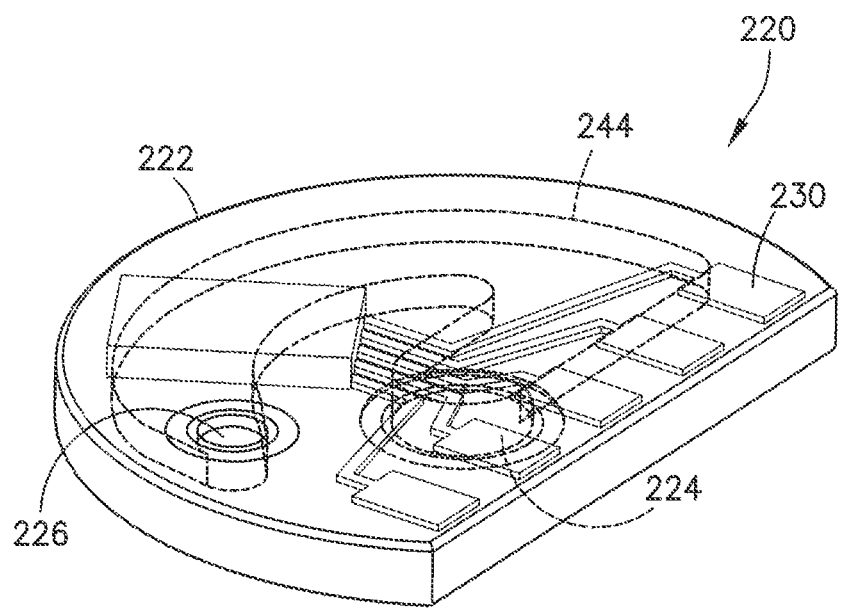
FIG. 16 illustrates a transparent perspective view of the flow sensor.

According to one embodiment, the electronic exchange system 200 further includes a flow sensor 220. The flow sensor 220, as illustrated in FIGS. 14-16, include a flow sensor housing 222 that houses the electrical components of the flow sensor 220. Medicament travels through a flow path 244 in the flow sensor 220 by entering via a sensor inlet 224 and exiting via a sensor outlet 226.

As illustrated in FIG. 3, the sensor inlet 224 is centered along a longitudinal edge of the flow sensor housing 222 and is aligned with the hollow spike 204 of the hub 202 in the electronic exchange system 200. The sensor inlet 224 includes a rubber seal or O-ring seal 228 that provides a hermetic or leak free interface between the flow sensor 220 and the hub 202. Such a configuration advantageously prevents medicament from contacting electrical components in the electronic exchange system 200. The sensor outlet 226 engages an upper septum 270 to establish fluid communication as described below.

The flow sensor 220 is advantageously configured so that there is no direct fluid contact between the medicament and a sensor chip or other electrical components. Instead, the flow path 244 routes the medicament through the flow sensor housing 222 to measure and extract the necessary medicament flow data. Preferably, the flow sensor 220 is a Sensirion LPG10 flow sensor.

The flow sensor 220 further includes electrical contacts 230. The electrical contacts 230 are disposed on an external surface of the flow sensor housing 222 to communicate flow data. In the electronic exchange system 200, the flexible circuit board 250 is electrically connected to the flow sensor housing 222 of the flow sensor 220 to receive and analyze the medicament flow data.

Figure 17:
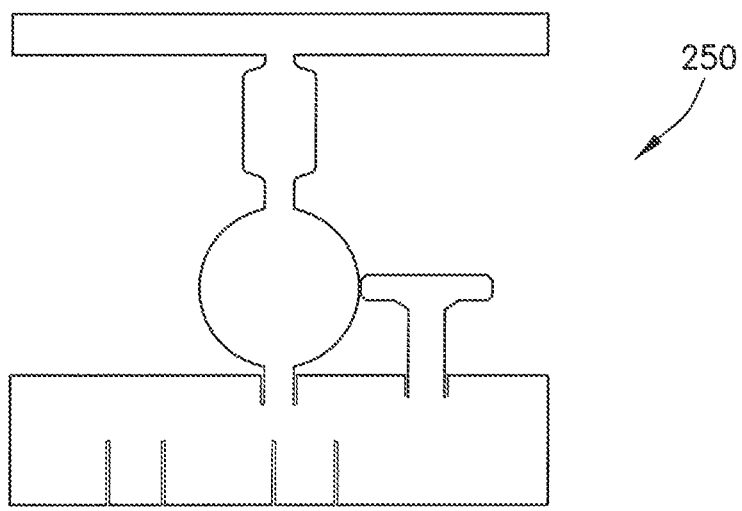
FIG. 17 illustrates a top view of a flexible circuit board in an unfolded position.
Figure 18:
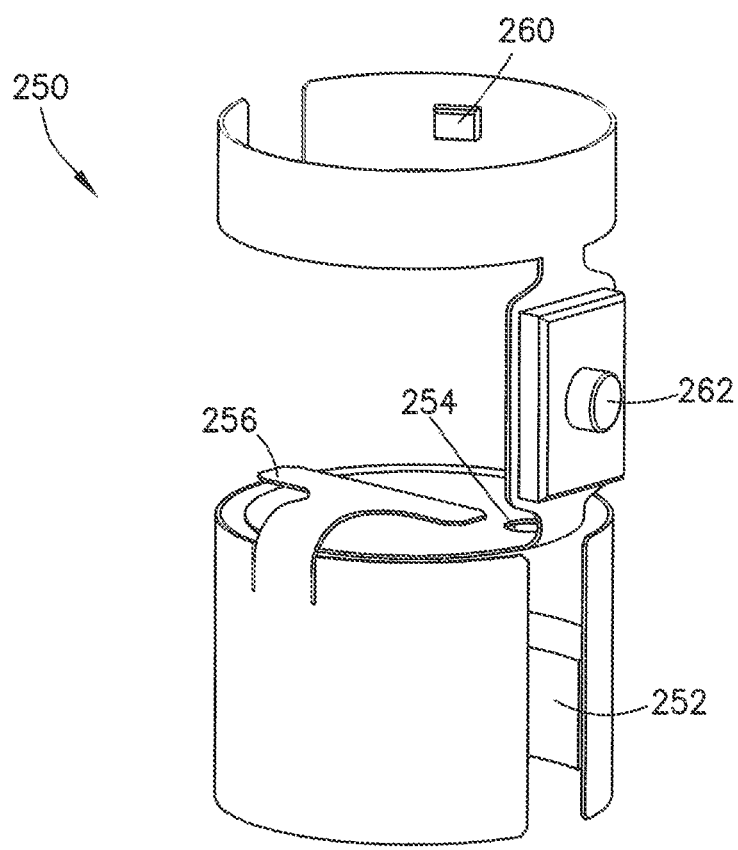
FIG. 18 illustrates a left perspective view of the flexible circuit board in the folded position.
Figure 19:
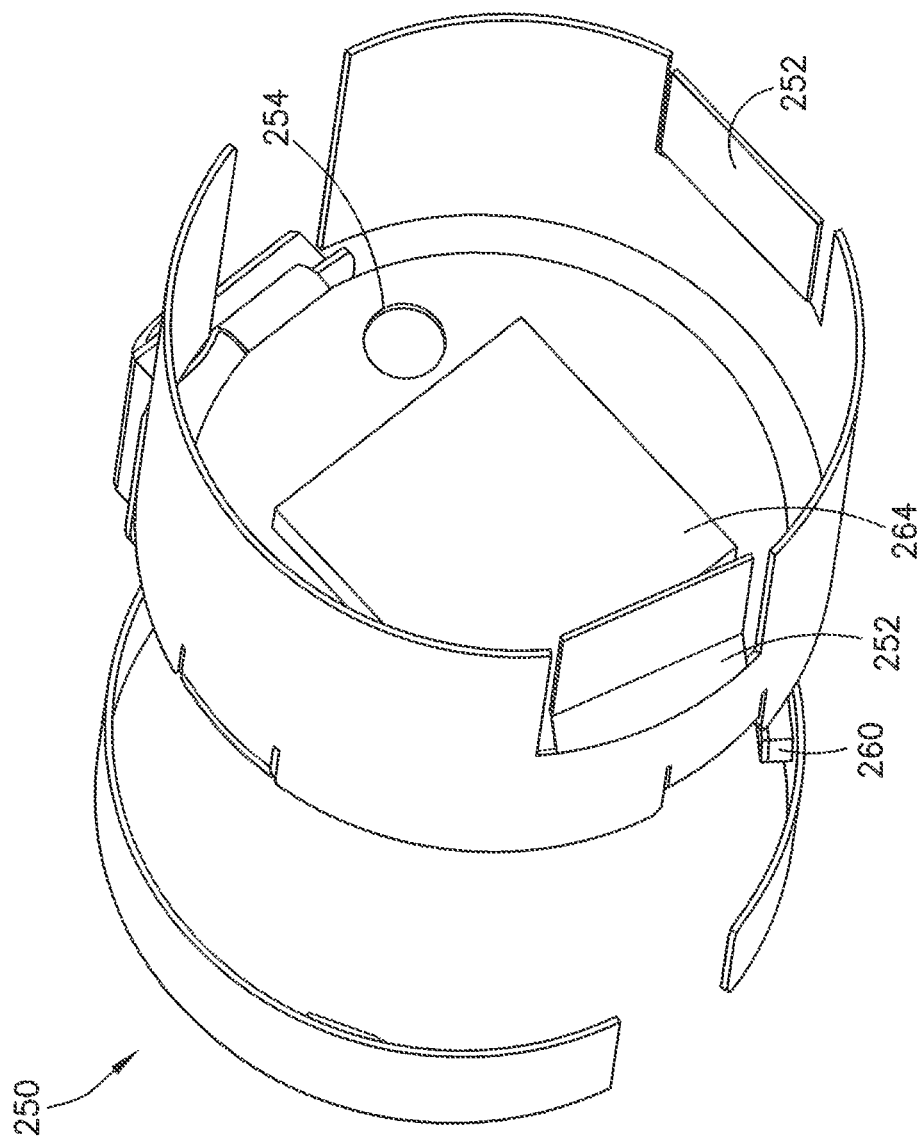
FIG. 19 illustrates a bottom left perspective view of the flexible circuit board in the folded position.
Figure 20:
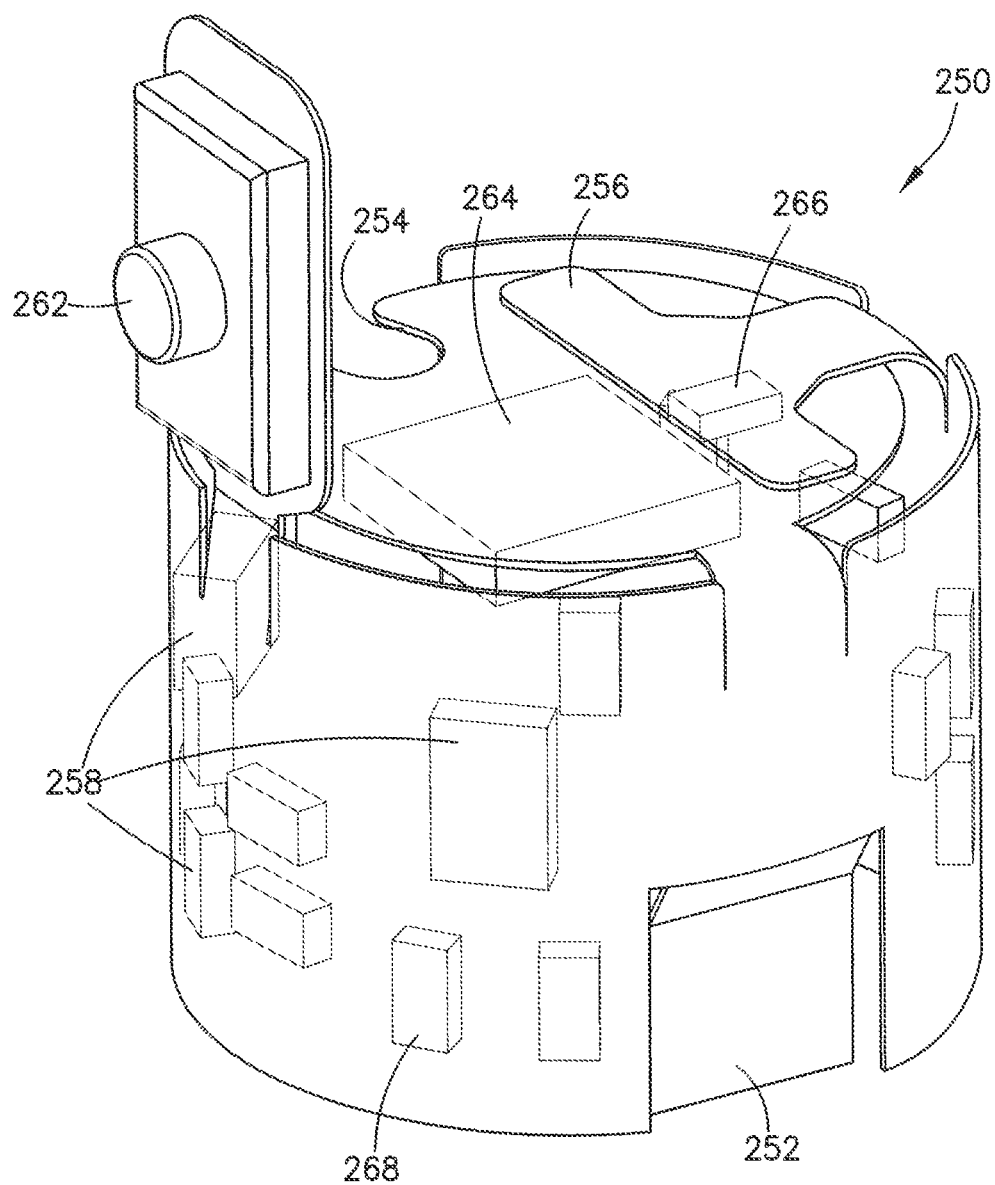
FIG. 20 illustrates a right perspective view of the flexible circuit board in the folded position.

The electronic exchange system 200, according to one embodiment, also includes the printed circuit board 250. Preferably, the printed circuit board 250 is a flexible circuit board. FIG. 17 illustrates the flexible circuit board 250 in a flat condition prior to folding (unfolded position), whereas FIGS. 18-20 illustrate the flexible circuit board 250 in its operational condition after folding (folded position). As illustrated in FIG. 3, the flexible circuit board 250 in the folded position in the electronic exchange system 200 advantageously provides a compact arrangement of electronics. The following components of the flexible circuit board 250 are described in view of the folded position.

The flexible circuit board 250 includes battery connector pads 252 that electrically connect to battery contacts 238 of a battery 236 as illustrated in FIGS. 13 and 18-20. The battery 236 is preferably a flexible battery with a step-up converter to increase voltage. Alternately, the battery 236 includes two flexible batteries stacked together in series, each with a voltage capacity of approximately three volts, for example.

The battery 236 advantageously aids to provide a compact arrangement of electronics in the electronic exchange system 200. Preferably, the battery 236 includes three battery contacts 238. The battery contacts 238 of the battery 236 are spaced apart from each other in a circumferential direction and disposed at a distal end of the battery 236. The battery 236 surrounds the flexible circuit board 250 by approximately 315° when assembled in the electronic exchange system 200.

The battery connector pads 252 are also spaced apart from each other in a circumferential direction and disposed at a distal end of the flexible circuit board 250. The battery contacts 238 of the battery 236 align and contact the battery connector pads 252 of the flexible circuit board 250. The battery 236 provides electrical energy for the electronic components in the electronic exchange system 200 to operate.

The flexible circuit board 250 further includes a fluid path hole 254. Alternatively, the fluid path hole 254 is a cutaway portion at a circumferential edge of the flexible circuit board 250. As illustrated in FIGS. 3 and 18-20, the fluid path hold 254 is disposed on a horizontal surface of the flexible circuit board 250. Specifically, as illustrated in FIG. 3, the horizontal surface of the flexible circuit board 250 is disposed between the flow sensor 220 and the upper septum 270. The fluid path hole 254 advantageously allows the medicament flow to travel through the flexible circuit board 250. Specifically, the fluid path hole 254 allows the sensor outlet 226 to engage the upper septum 270. The fluid path hole 254 advantageously allows for a compact arrangement of electronics in the electronic exchange system 200 without inconveniently rerouting the flow path 244 around various components.

As described above, the flow sensor 220 is connected to the flexible circuit board 250 via a sensor connector pad 256. As illustrated in FIGS. 18 and 20, the sensor connector pad 256 is disposed horizontally and adjacent to the horizontal surface of the flexible circuit board 250 in the folded position. The sensor connector pad 256 is also disposed adjacent to the fluid path hole 254 and below the flow sensor 220. Accordingly, the sensor connector pad 256 aligns with the electrical contacts 230 of the flow sensor 220 when the exchange system 200 is assembled. In this manner, the flexible circuit board 250 advantageously receives the flow data from the flow sensor 220 for further analysis and processing. Moreover, such transfer of flow data from the flow sensor 220 to the flexible circuit board 250 advantageously occurs through a compact arrangement of electronics in the electronic exchange system 200.

As illustrated in FIG. 20, various circuit board components 258 are connected to the flexible circuit board 250. According to one embodiment, some of these components include a plurality of light emitting diodes (LEDs) 260, a tactile switch 262, a Bluetooth chip 264, a memory chip 266 and a microprocessor 268.

In an alternate configuration, a microprocessor and a memory chip included in a standard Bluetooth chip may be sufficient and not require these components separately on the flexible circuit board 250. In this instance, the Bluetooth chip will require various simple circuit elements such as resistors, capacitors and diodes to function properly.

The plurality of LEDs 260, as illustrated in FIGS. 18 and 19, preferably includes three LEDs 260. The LEDs 260 are disposed and spaced apart from each other on a circumferential surface of the flexible circuit board 250. The circumferential surface is disposed at a proximal end of the flexible circuit board 250. The LEDs 260 indicate device status.

For example, if the LEDs 260 are together illuminating solid light, the electronic exchange system 200 is powered on and ready for operation. If the LEDs 260 are together blinking, the medicament is being delivered and will continue to blink for ten seconds after the dose is delivered to the patient. If the LEDs 260 are together not illuminated, the electronic exchange system 200 is powered off. Alternately, the LEDs 260 can illuminate in different colors or individually to indicate device status. For example, the LEDs 260 can illuminate different colors to indicate various error conditions (clogging or low battery, for example), as well as pairing status with a Bluetooth enabled external device.

As described above, the LEDs 268 also indicate when the electronic exchange system 200 is paired to an external system such as a smart phone or a computer. Moreover, the LEDs 260 are illuminated during dosing to indicate flow status such as in "progress," "complete," "clogging," when the electrical communication is paired for real-time transfer of delivery data to the external system, and when the user can remove the delivery device needle (e.g., flow rate indicates injection is complete, or the microprocessor 268 determines the flow over a designated period of time matches an inputted dose amount), among other states.

Preferably, the hub 202 is translucent and configured to receive the light emitted from the LEDs 260. The hub 202 is configured to diffuse the light emitted by the LEDs 260 around an entire outer perimeter of the needle assembly 2 and the electronic exchange system 200. In this manner, the device status of the electronic exchange system 200 is more obvious from various viewing angles. Also, the device status of the electronic exchange system 200 is determined by the user based on illumination of the hub 202.

As illustrated in FIGS. 18 and 20, the tactile switch 262 is connected on a side surface of the flexible circuit board 250. The side surface is a vertical surface connecting the horizontal surface, including the fluid path hole 254, and the circumferential surface, including the plurality of LEDs 260, of the flexible circuit board 250. FIG. 3 illustrates that the tactile switch 262 is disposed within the hole in the frame pocket 212 of the frame 210. The tactile switch 262 extends through the hole of the frame pocket 212 so that the user can compress the tactile switch 262 to operate (i.e. activate and deactivate) the electronic exchange system 200.

As illustrated in FIGS. 19 and 20, the Bluetooth chip 264 is also disposed on the horizontal surface of the flexible circuit board 250. In the electronic exchange system 200, the Bluetooth chip 264 is disposed above and adjacent to the upper septum 270. The Bluetooth chip 264 provides data communication between the electronic exchange system 200 and the external system. Alternatively, Wi-Fi technology can be used in place of the Bluetooth chip 264 for similar purposes.

FIG. 20 illustrates the memory chip 266 disposed on the horizontal surface of the flexible circuit board 250. The memory chip 266 stores information when the flow data or any processed information is not transferred to the external system.

According to an alternate embodiment, data provided during or immediately after injection from the electronic exchange system 200 is automatically transferred and stored at a memory device in the external system with a time stamp using a clock in the external system. In this manner, the electronic exchange system 200 does not process the flow data. Instead, while dosing is in progress, the external system can be configured by an app, for example, to receive and process flow data to determine flow rate over time, total dose and other flow and dosing characteristics.

FIG. 20 also illustrates the microprocessor 268 disposed on the flexible circuit board 250. The microprocessor 268 provides the following functional advantages and benefits. The microprocessor 268 receives a desired dose from the user via the Bluetooth chip 264 and analyzes the flow data received from the flow sensor 220 to determine a dose delivery completion status. The microprocessor 268 measures time through a global positioning system (GPS) or alternatively includes a real time clock (e.g., Abracon AB-RTCMC real-time clock module or equivalent thereof). The microprocessor 268 uses this time data to determine rate of delivery and time of delivery completion. When the dosing is being administered, the microprocessor 268 receives flow data from the flow sensor 220 and determines how much time is needed to deliver the desired dose, total dose delivered, dose time, dose rate, or dose status such as "in progress" or "complete." Additionally, flow data during delivery indicates issues such as clogging and generates user alerts during dosing. The microprocessor 268 also calculates a dose history for the user to access.

The microprocessor 268 transfers the data regarding drug delivery status (e.g., complete or in progress, as described above) or other delivery information (e.g., rate, timing, as described above) in real-time (e.g., during injection) or at any time such as after injection. For example, the electronic exchange system 200 captures time of dose and sends timing information with flow and total amount delivered data to the external system. This transfer occurs via the Wi-Fi technology or the Bluetooth chip 264 as described above.

According to one embodiment, the foam pad 240 has a cylindrical shape similar to the flexible battery 236. However, the foam pad 240 is tubular shaped. The foam pad 240 is adjacent to the hub 202 and the flow sensor 220 at an inner diameter surface of the foam pad 240. The foam pad 240 is also adjacent to the flexible battery 236 and the flexible circuit board 250 at an outer diameter surface of the foam pad 240. Thus, the foam pad 240 is advantageously disposed between various components of the electronic exchange system 200.

The foam pad 240 advantageously provides a small force when compressed. The arrangement of components in the electronic exchange system 200 as illustrated in FIG. 3, compresses the foam pad 240 resulting in a compression force. Accordingly, the tactile switch 262 of the flexible circuit board 250 receives the compression force from the foam pad 240. This compression force ensures that the tactile switch 262 protrudes out of the hole in the pocket 212 of the frame 210 throughout operation of the electronic exchange system 200.

Figure 21:
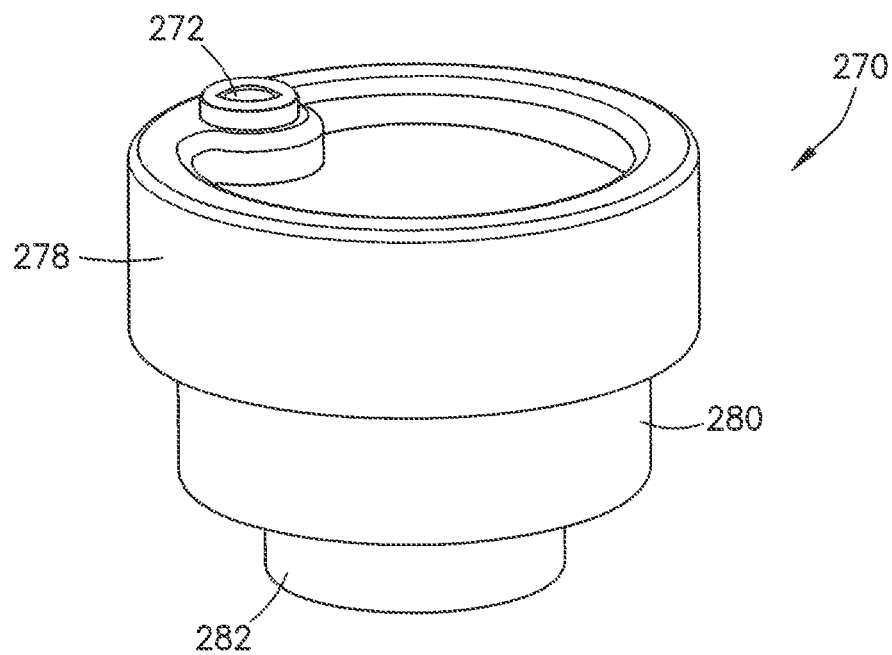
FIG. 21 illustrates a front perspective view of an upper septum.
Figure 22:
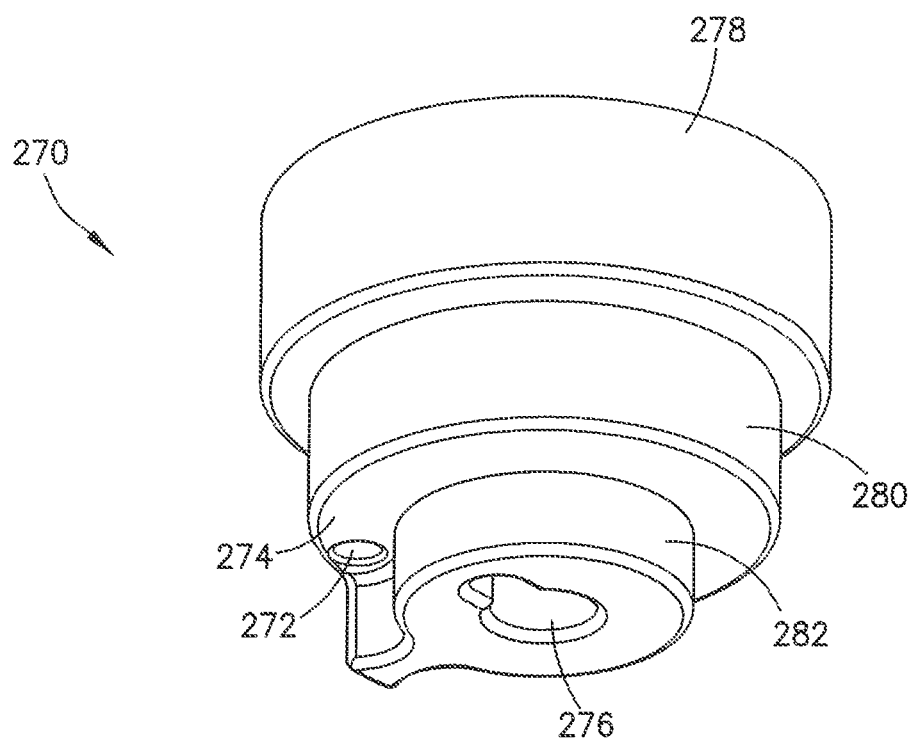
FIG. 22 illustrates a bottom perspective view of the upper septum.

According to one embodiment, the electronic exchange system 200 further includes the upper septum 270 and the lower septum 284 (generally together referred to as septum body 270/284). FIGS. 21 and 22 illustrate the upper septum 270 including an input chamber 272 being a through hole. The input chamber 272 is offset from and not in-line with the center of the upper septum 270. A proximal end of the input chamber 272 connects to the sensor outlet 226 of the flow sensor 220. A distal end of the input chamber 272 is in fluid communication with a delivery chamber 274. The input chamber 272 allows liquid medicament to flow from the medication delivery pen 4 and to the delivery chamber 274.

The delivery chamber 274 is formed when the upper and lower septums 270, 284 are joined together. Specifically, the upper septum 270 further includes a first diameter 278, a second diameter 280 and a third diameter 282. The first diameter 278 is the largest of the three diameters that covers the lower septum 284. The delivery chamber 274 is disposed between outer surfaces of the second and third diameters 280, 282 of the upper septum 270. Further details of the delivery chamber 274 are described below.

The upper septum 270 further includes an alignment keyhole 276. The alignment keyhole 276 is disposed at a distal end of the upper septum 270. The alignment keyhole 276 is a partially extruded hole and key slot at a bottom face of the third diameter 282. The alignment keyhole 276 mates with a corresponding alignment protrusion 286 in the lower septum 284 for proper orientation of the upper and lower septums 270, 284.

Figure 23:
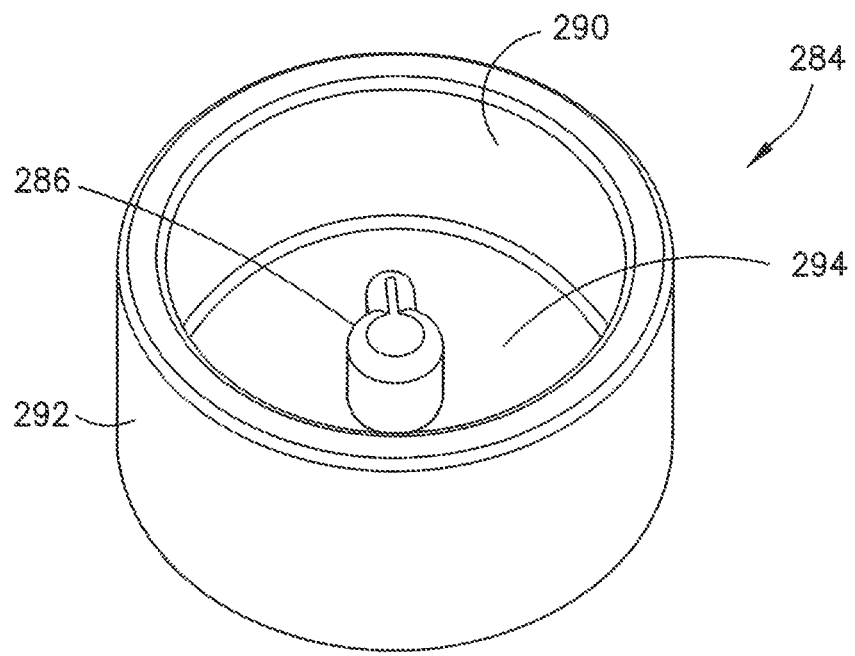
FIG. 23 illustrates a top perspective view of a lower septum.
Figure 24:
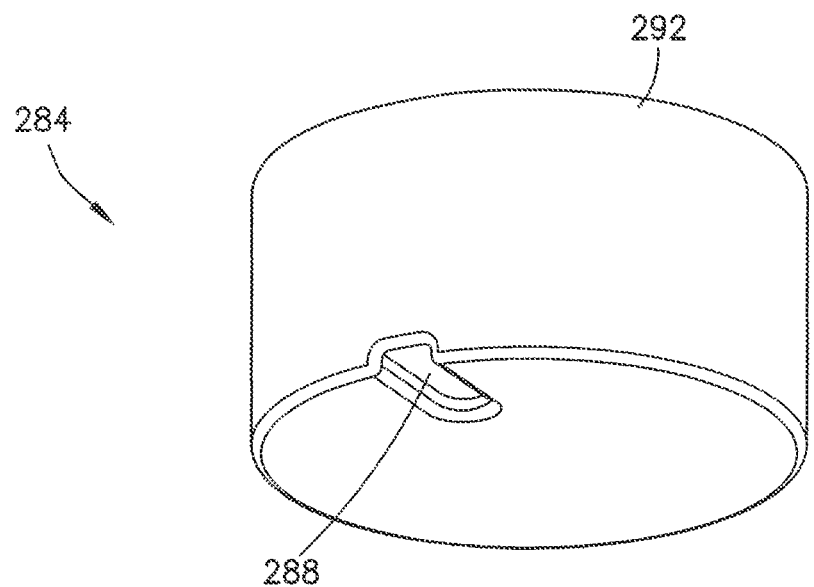
FIG. 24 illustrates a bottom perspective view of the lower septum.

The lower septum 284 or priming septum is illustrated in FIGS. 23 and 24. The lower septum 284 includes the alignment protrusion 286 that mates with the alignment keyhole 276 of the upper septum 270 as described above. The alignment protrusion 286 extends from a bottom inner surface 294 of the lower septum 284.

The lower septum 284 also includes the groove, recess or extruded key 288 disposed at an exterior bottom surface of the lower septum 284. As described above, the groove 288 mates with the protruding key 216 located at the bottom inner surface of the frame 210. This feature orients the lower septum 284 and the delivery chamber 274 to the frame 210 for proper operation.

The lower septum 284 further includes an inner diameter 290 and an outer diameter 292. The inner diameter 290 mates with the second diameter 280 of the upper septum 270 and provides direct sealing contact. The delivery chamber 274 is thus formed within the inner diameter 290 and above the bottom inner surface 294 of the lower septum 284, as well as outside the third diameter 282 and below bottom surface of the second diameter 280 of the upper septum 270. The input chamber 272 is aligned to be in fluid communication with the delivery chamber 274. Thus, the delivery chamber 274 stores the medicament received from the input chamber 272 for medication delivery via an exemplary needle assembly.

The upper septum 270 is secured to the lower septum 284 via an annular snap fit or an interference fit, for example. The upper septum 270 and the lower septum 284 are preferably composed of different materials having different durometers. Such characteristics enhance sealing between the second diameter 280 of the upper septum 270 and the inner diameter 290 of the lower septum 284.

Figure 25:
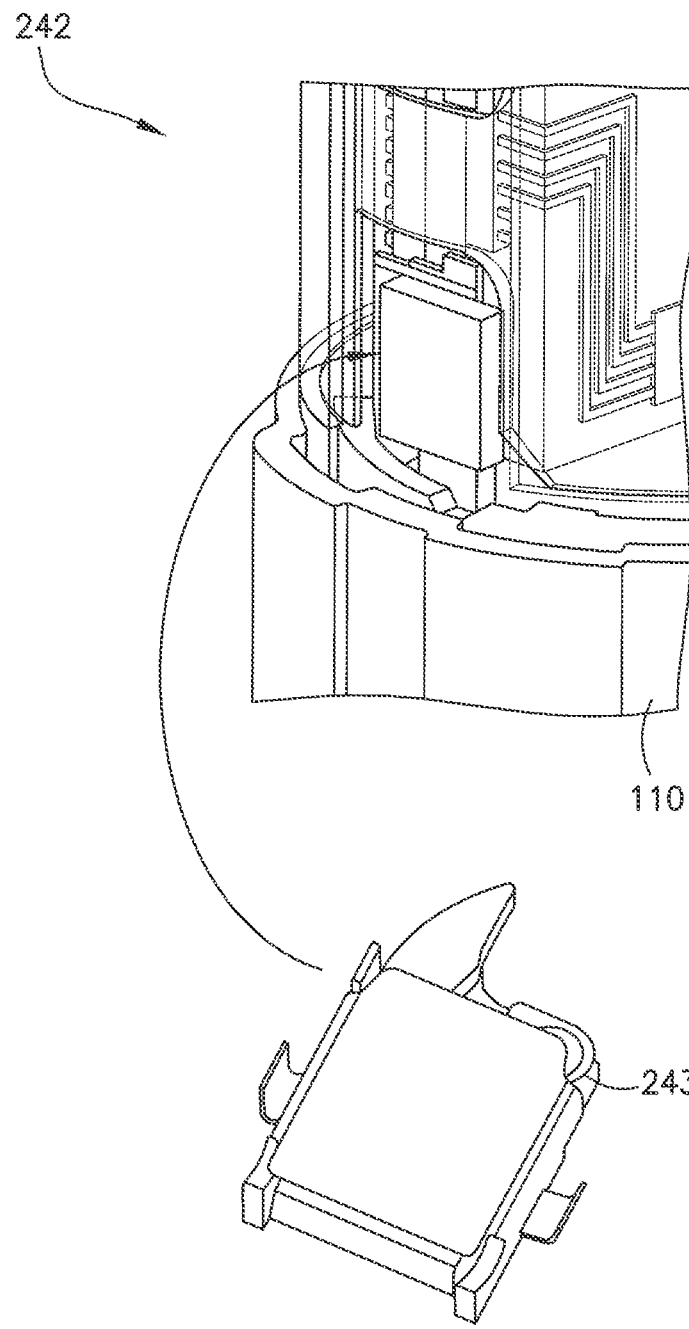
FIG. 25 illustrates an electronic exchange system including an activation switch being a detector switch.
Figure 26:
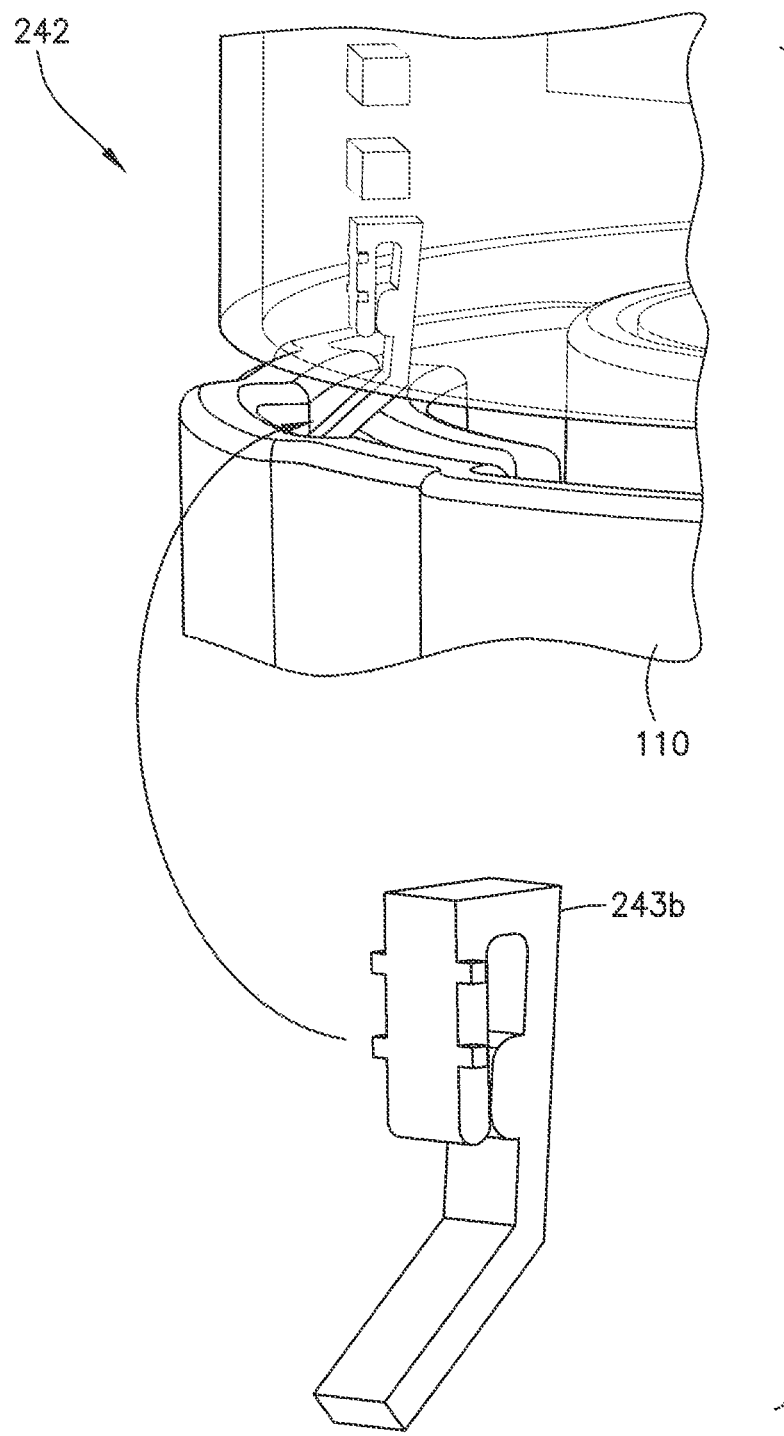
FIG. 26 illustrates an electronic exchange system including an activation switch being a tactile switch.

The electronic exchange system 200, according to one embodiment, can provide alternate means for activation instead of using the tactile switch 262 in the flexible circuit board 250. FIGS. 25-27 illustrate various activation switches 242. Each of the activation switches 242 are initiated when the user moves a housing 110 of the needle assembly 102, as described further below. When the activation switch 242 is turned on, the LED 260 is illuminated in a similar manner as described above to show readiness of the electronic exchange system 200.

FIG. 25 illustrates the activation switch 242 being a detector switch 243a. The detector switch 243a will detect and determine when the housing 110 covers a predetermined portion of the electronic exchange system 200 to activate the electronic exchange system 200. FIG. 26 illustrates the activation switch 242 being a flanged switch 243b. When the housing 110 moves and covers a predetermined portion of the electronic exchange system 200, the flanged switch 243b deflects and thus activates the electronic exchange system 200. FIG. 27 illustrates the activation switch 242 being a Hall Effect sensor 243c. The Hall Effect sensor 243c includes a magnet and a Hall Effect switch. The magnet is disposed in the housing 110 and the Hall Effect switch is disposed on an exterior surface of the electronic exchange system 200. When the housing 110 moves and aligns the magnet to the Hall Effect switch, the Hall Effect sensor 243c activates the electronic exchange system 200.

FIG. 27B illustrates a block diagram showing the operation of the flexible circuit board 250 in the magazine electronic exchange system 200. Specifically, the memory chip 266, the activation switch 242, the power source and regulation (i.e. the flexible battery) 236 and the flow sensor 220 cooperate with the microprocessor 268 for appropriate operation as described above. The microprocessor 268 also communicates with the wireless module Bluetooth chip) 264 and the tactile switch 262 for efficient power usage and transfer of data.

Figure 4:
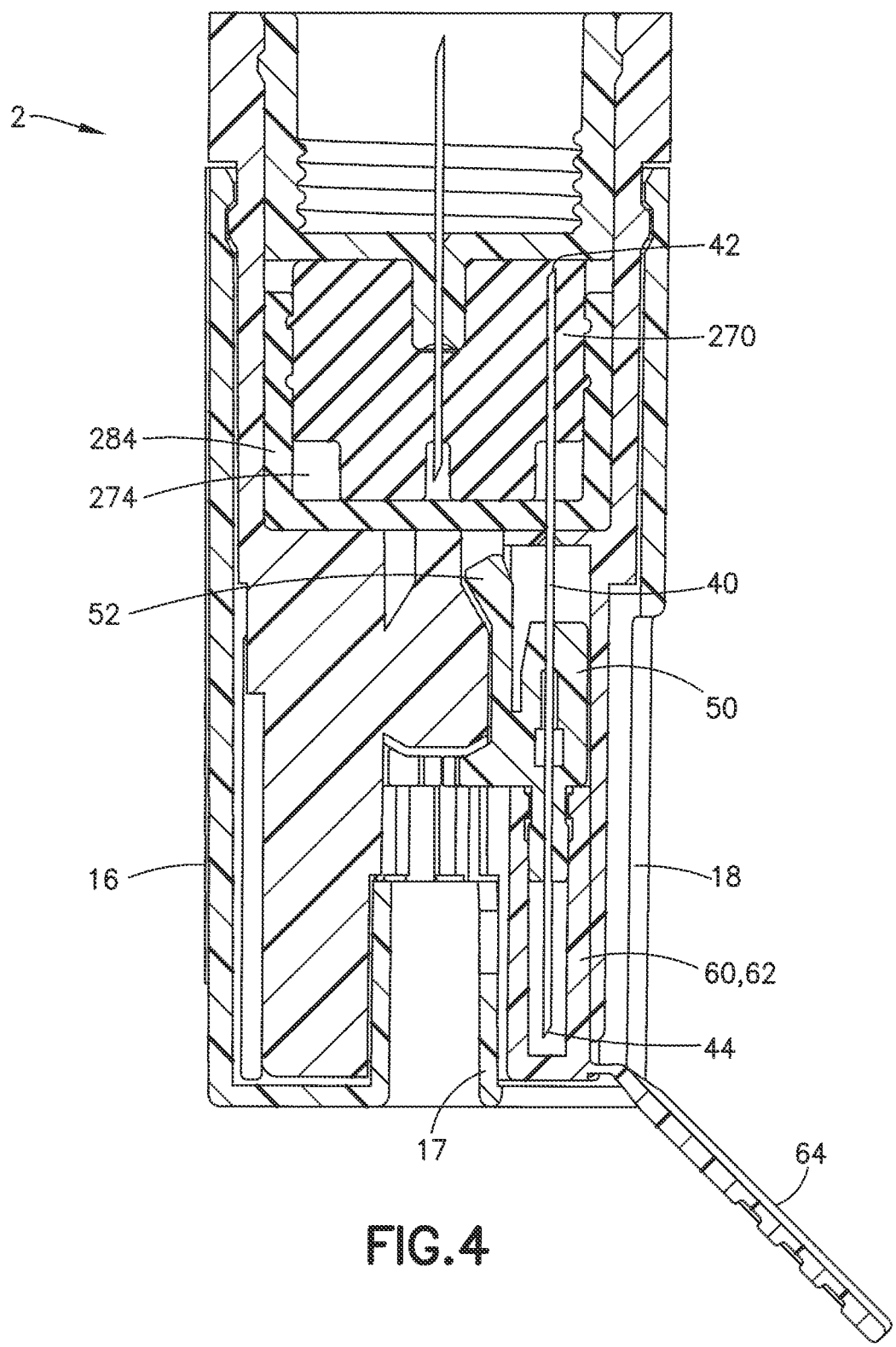
FIG. 4 illustrates a cross sectional view of the needle assembly connected to the electronic exchange system in a first position.

FIGS. 1a, 1b, 2, 4 and 5, according to one embodiment, illustrate the needle assembly 2 that connects to the electronic exchange system 200. Specifically, a sharpened proximal end 36 of the plurality of hollow needles 34 is disposed in the upper septum 270 in a first position of the needle assembly 2 as illustrated in FIG. 4. The plurality of needles 34 extends through the delivery chamber 274, thus contacting the medicament. However, the plurality of needles 34 is not in fluid communication with the delivery chamber 274.

Figure 5:
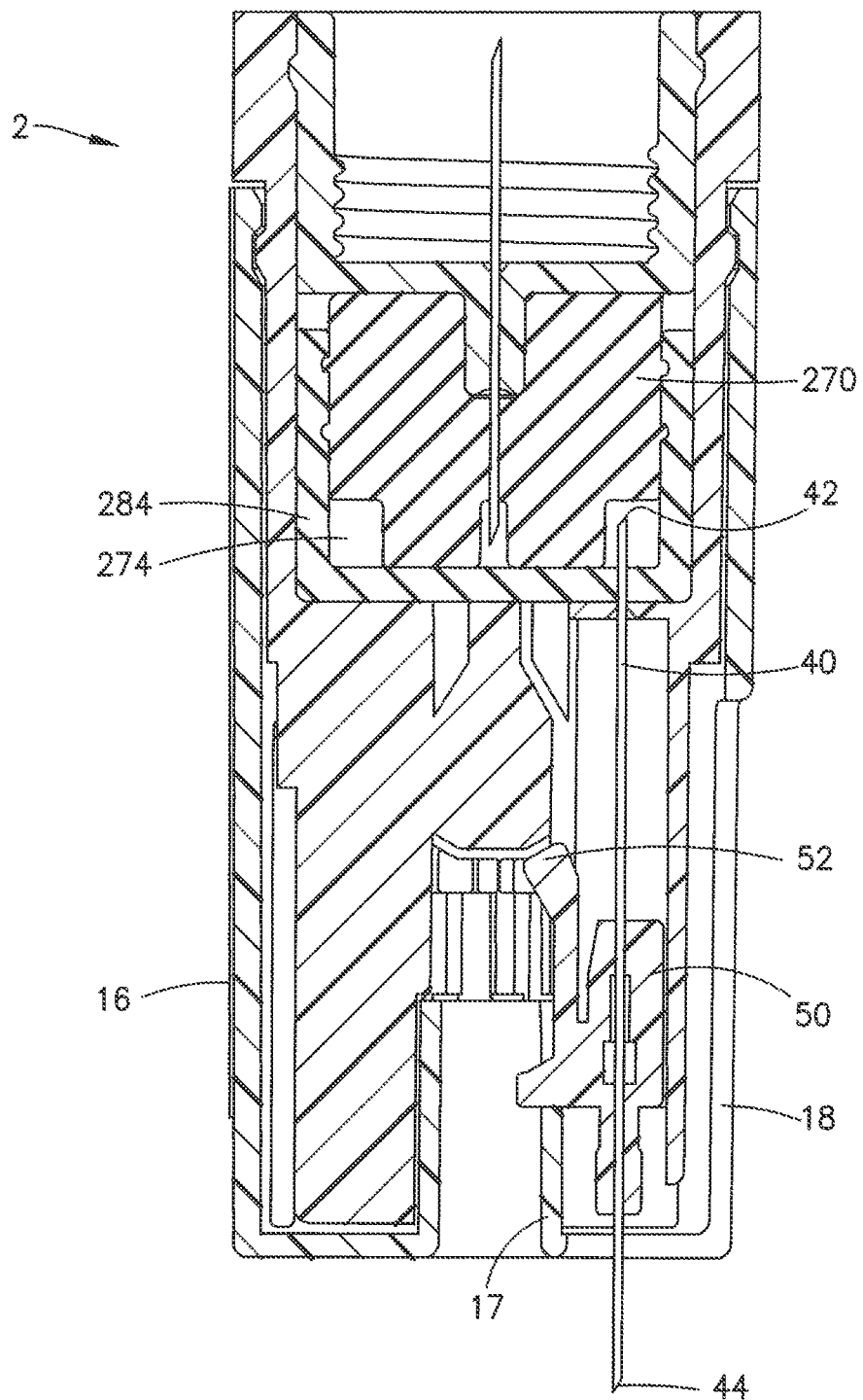
FIG. 5 illustrates a cross sectional view of the needle assembly connected to the electronic exchange system in a second position.

In a second position of the needle assembly 2, as illustrated in FIG. 5, one of the plurality of needles 34 is exposed for medicament delivery. In this instance, a proximal end 42 of a selected needle 40 is disposed in the delivery chamber 274 to receive medicament. A distal end 44 of the selected needle 40 is exposed for medication delivery.

The operation of the needle assembly 2 connected to the electronic exchange system 200 is now explained in an exemplary manner as follows. According to one embodiment, the user aligns and connects the needle assembly 2 to the electronic exchange system 200. When the user desires to use the needle assembly 2 for medication delivery, the selector ring 16 is rotated to align with a peel tab 60 as illustrated in FIGS. 1a, 1b and 2. As illustrated in FIGS. 4 and 5, the user bends the tab 64 of the peel tab 60 of the selected needle 40 from a retracted, compact position to an extended position.

Next, the user pulls the tab 64 of the peel tab 60 of the selected needle 40 and moves the needle assembly 2 from the first position of FIG. 4 to the second position of FIG. 5. When the selected needle 40 is fully drawn out, the needle assembly 2 is in the second position. Subsequently, the sterility barrier 60 is removed from the selected needle 40 and the needle assembly 2 is ready for medicament delivery. When the needle assembly 2 moves from the first position to the second position, the needle post 50 of the selected, needle 40 moves from a top position to a bottom position.

In the second position of the needle assembly 2, a proximal end 42 of the selected needle 40 also enters into fluid communication with the delivery chamber 274 of the electronic exchange system 200. A distal end 44 of the selected needle 40 exits the selector ring 16 and is exposed for medication delivery. Accordingly, medicament is received by the proximal end 42 of the selected needle 40 and exits the distal end 44 of the selected needle 40 to be delivered to a patient.

When the first needle of the plurality of needles 34 is used, the delivery chamber 274 is filled with medicament, resulting in the needle assembly septum 270, 284 being primed. Specifically, medicament must traverse and fill the complete fluid path of the delivery chamber 274 to reach the first needle of the plurality of needles 34. Accordingly, the incidence of air in the delivery chamber 274 is advantageously reduced. Removing air from the fluid path also advantageously improves dose accuracy.

Figure 6:
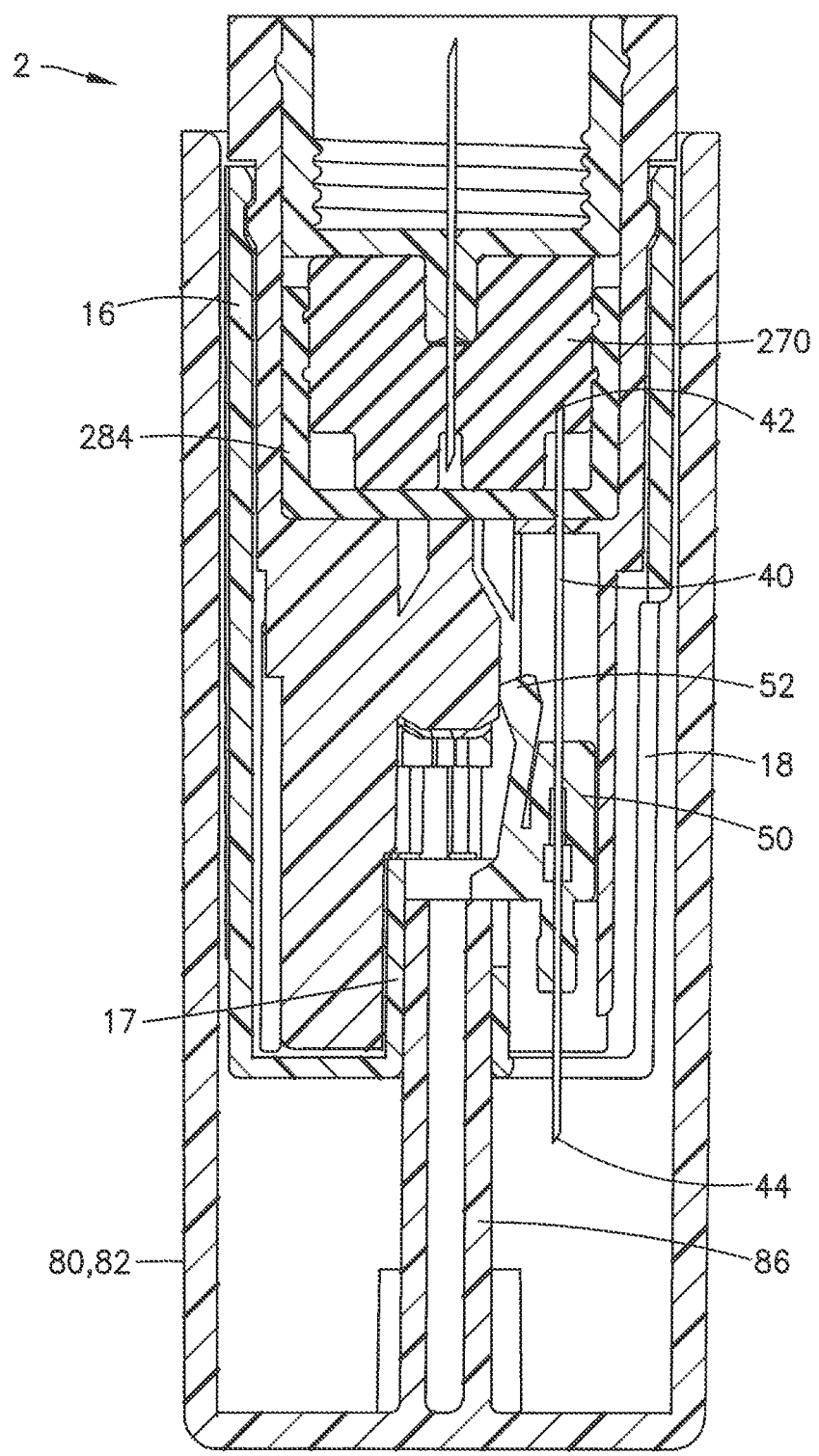
FIG. 6 illustrates a cross sectional view of the needle assembly connected to the electronic exchange system with a cover moving the needle assembly from the second position to the first position.
Figure 7:
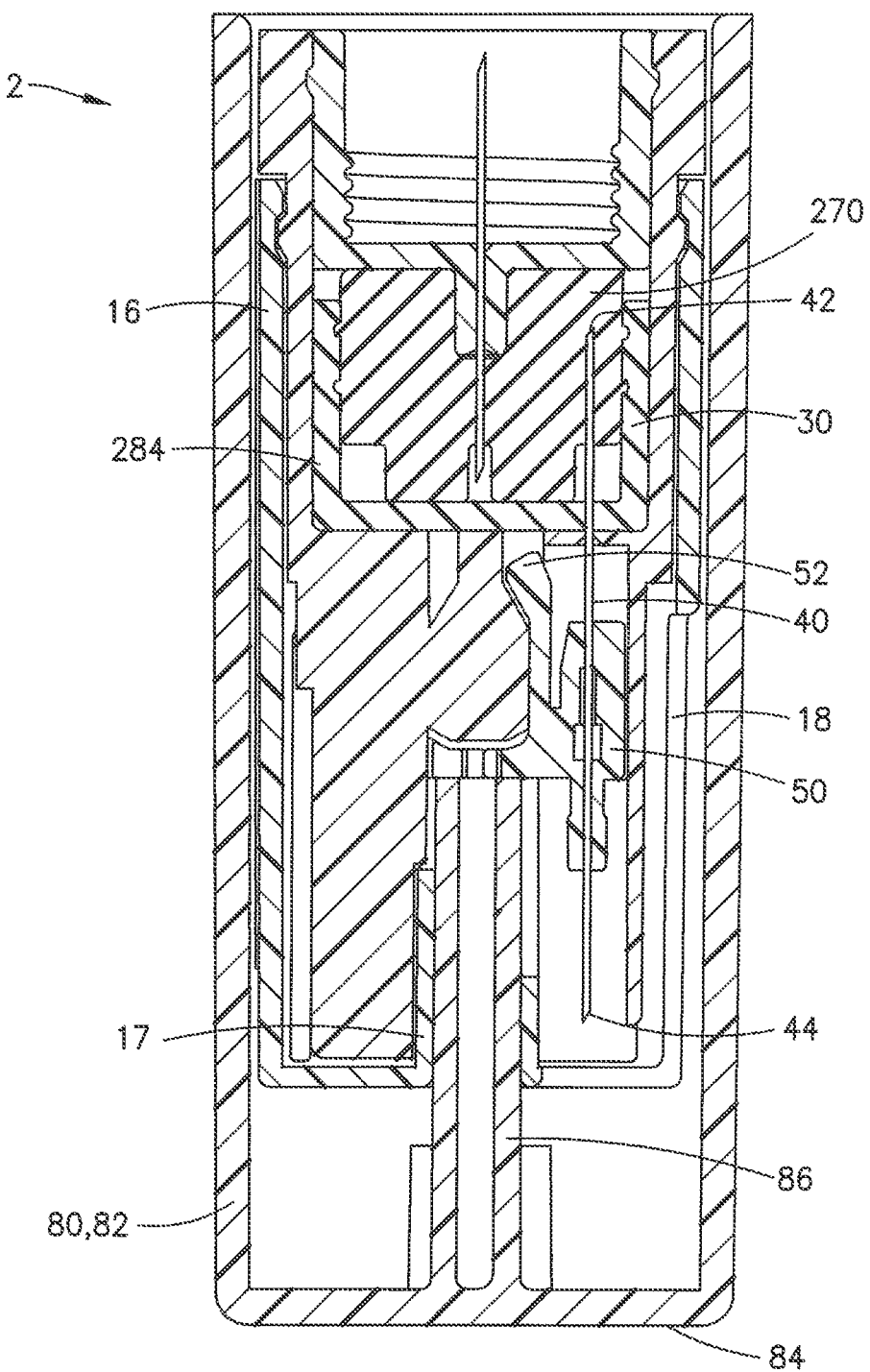
FIG. 7 illustrates a cross sectional view of the needle assembly connected to the electronic exchange system with the cover disposed in the first position of the needle assembly.

FIGS. 6 and 7, according to one embodiment, illustrate the use of a cover 80 to return the needle assembly 2 from the second position to the first position. The cover 80 includes a cylinder 82, a base 84 and a protrusion 86. The cylinder 82 is configured to surround the needle assembly 2. The base 84 is configured to cover a bottom portion of the selector ring 16 of the needle assembly 2. The protrusion 86 extends from the base 84 and is disposed centrally within the cylinder 82. When the cover 80 is placed on the needle assembly 2, the protrusion 86 enters a selector hole 17 in the selector ring 16. The protrusion 86 of the cover 80 applies pressure by pushing the needle post flange 52 of the needle post 50 of the selected needle 40 from the bottom position to the top position.

FIG. 6 illustrate the needle assembly 2 moving from the second position to the first position and FIG. 7 illustrates the second position of the needle assembly 2. These figures also illustrate that the needle post flanges 52 of each of the plurality of needles 34 are arranged toward a central axis of the selector ring 16. Such a configuration advantageously allows the protrusion 86 of the cover 80 to engage each of the plurality of needle posts flanges 52 in the selector hole 17 to move the needle post 50 from the bottom position to the top position.

After the needle assembly 2 is returned to the first position, according to one embodiment, an adjacent needle is preferably selected for use. The selector ring 16 is then rotated to expose an adjacent peel tab 60 of the adjacent needle. However, the user has the flexibility to expose and choose any of the remaining plurality of peel tabs 60.

Once a needle and respective peel tab 60 is selected, the selected peel tab 60 is removed for operation in the manner described above. The selected needle 40 is then used for medication delivery and afterwards, the cover 80 is used to return the selected needle 40 to the first position of the needle assembly 2. These steps are repeated until all of the plurality of needles 34 is used. The combination of the selector ring 16 and the plurality of peel tabs 60 simplify the needle assembly 2, allow for easy to use operation and improve safety.

Each of the plurality of needles 34 is advantageously isolated from the septum of the medication delivery pen 4 throughout the operation of the electronic exchange system 200 and the needle assembly 2. Also, the needle assemblies 2, 102 can include a USB port to transfer data. Such an arrangement advantageously provides simplicity in design, improves sterility, allows data transfer and provides a separation between a patient end and a non-patient end.

Figure 28:
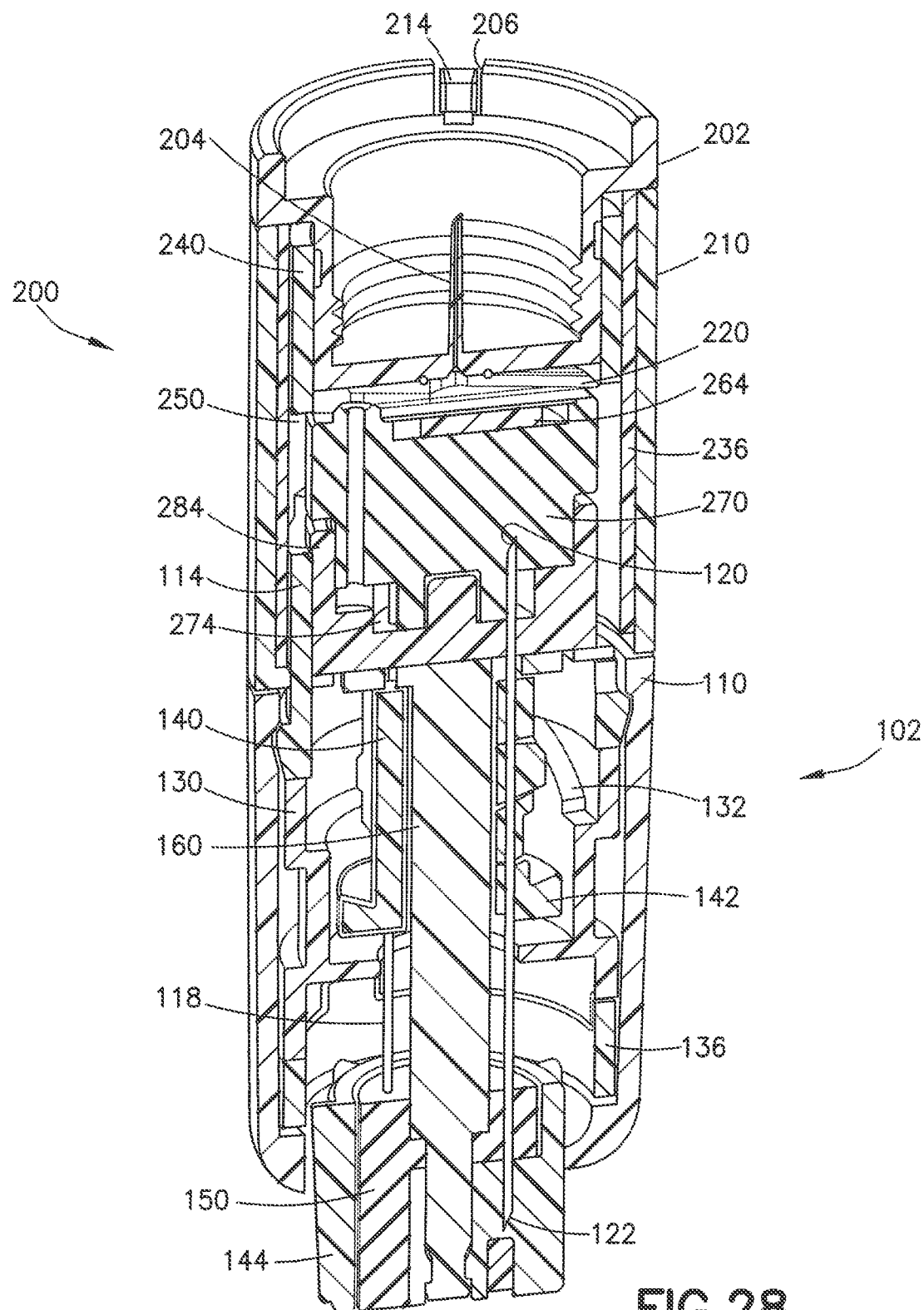
FIG. 28 illustrates a cross sectional view of an electronic exchange system connected to another embodiment of the needle assembly in a first position.
Figure 29:
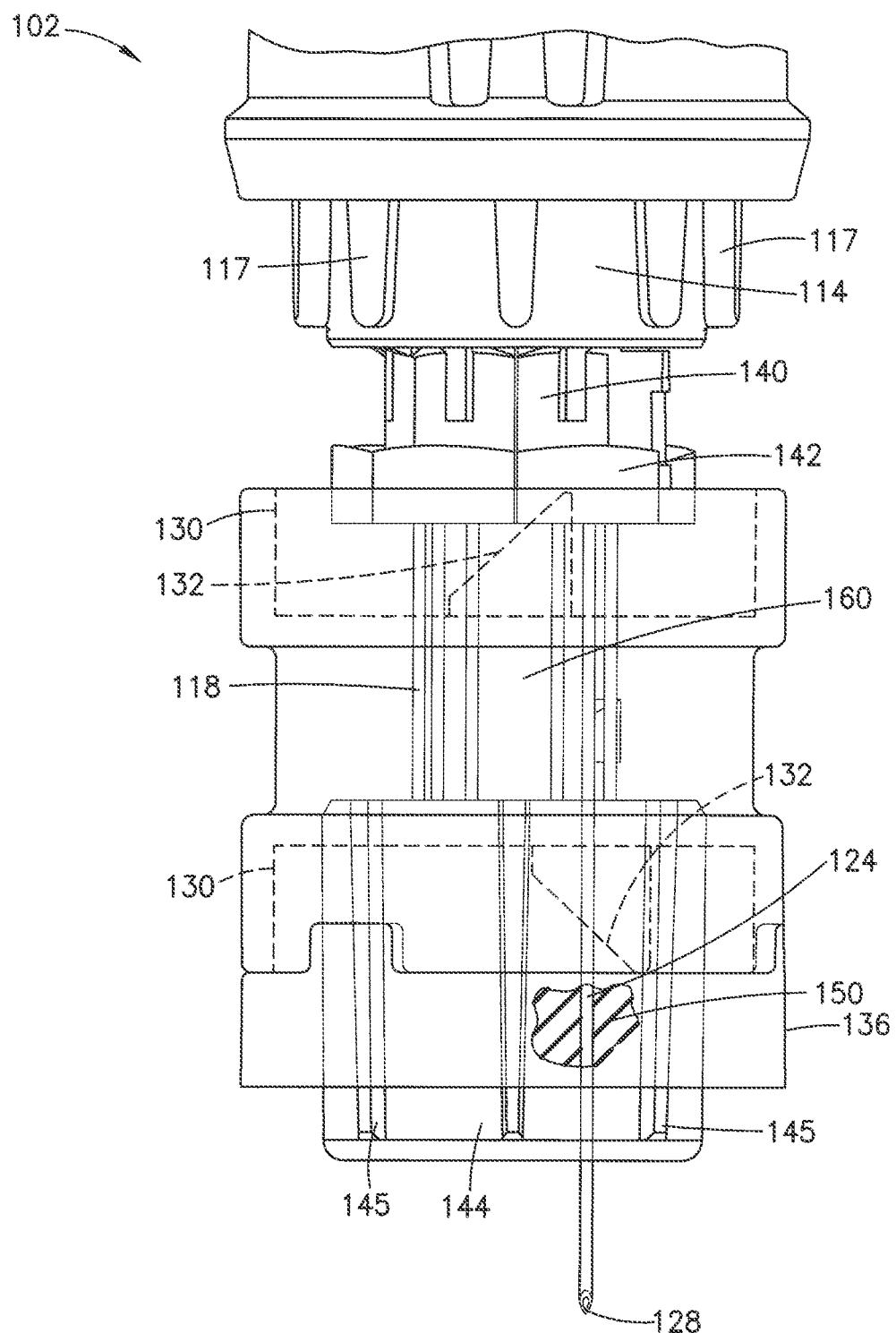
FIG. 29 illustrates a perspective view of an electronic exchange system connected to the embodiment of the needle assembly of FIG. 28 in a second position.
Figure 31:
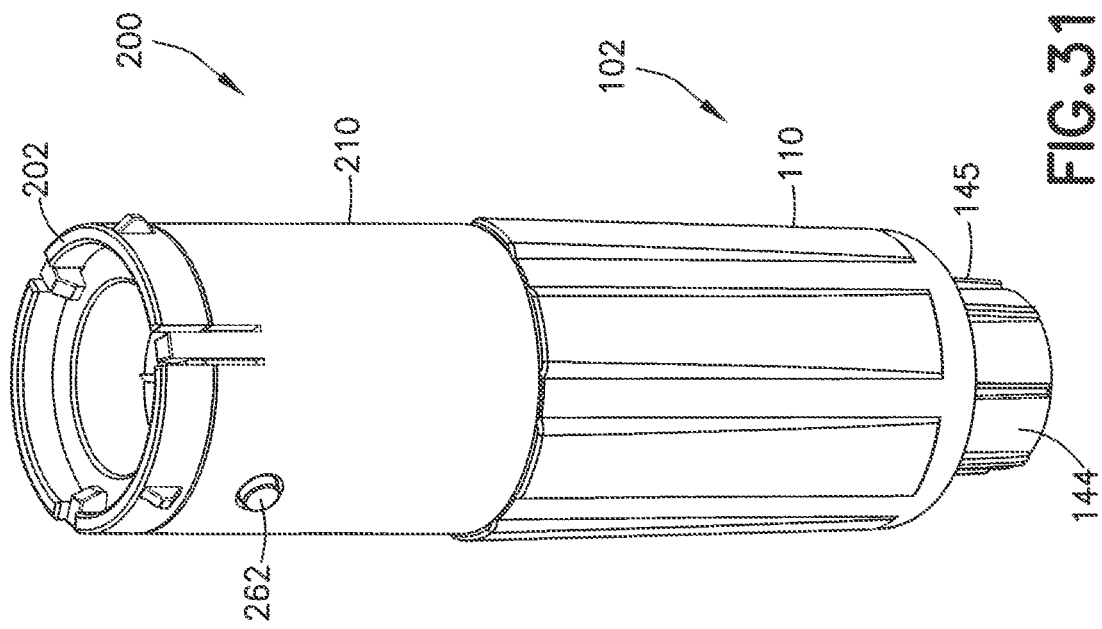
FIG. 31 illustrates a front perspective view of the electronic exchange system connected to the needle assembly of FIG. 28.
Figure 30:
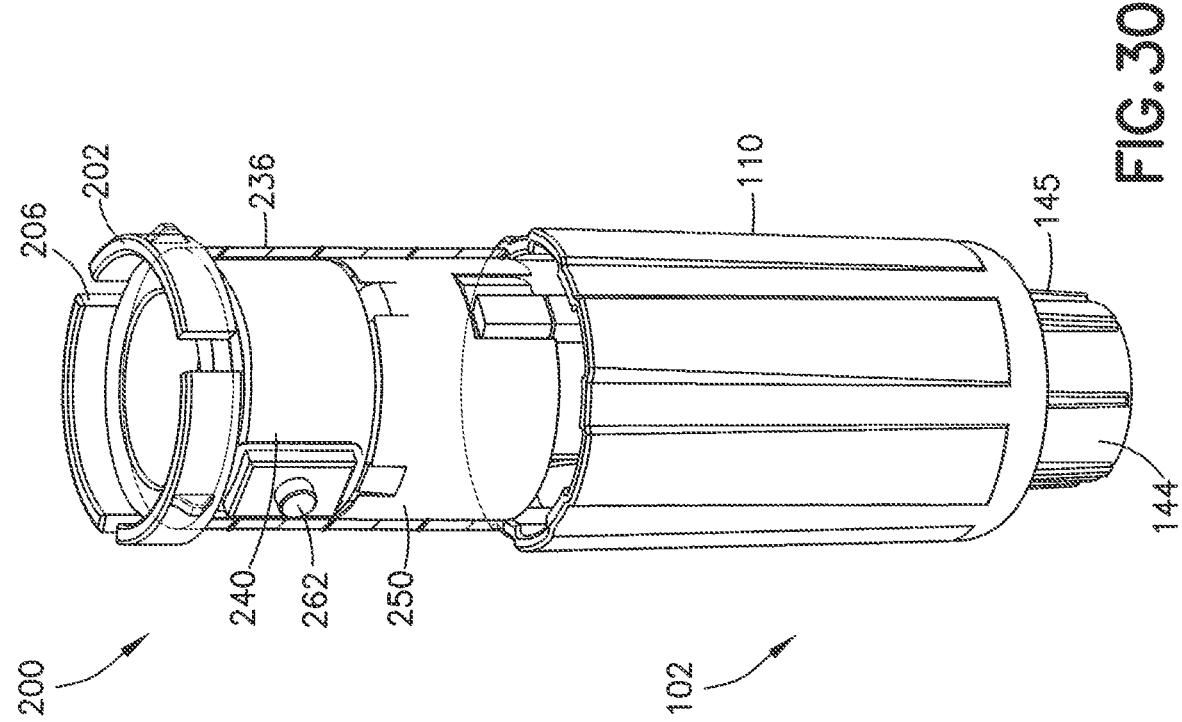
FIG. 30 illustrates a front perspective view of the electronic exchange system connected to the needle assembly of FIG. 28 with the frame removed.

FIGS. 28-31 illustrate the electronic exchange system 200 cooperating with another exemplary needle assembly 102. The following describes the operation of the needle assembly 102. According to one embodiment, the needle assembly 102 moves from a first position, as illustrated in FIG. 28, and toward a second position, as illustrated in FIG. 29, where a sharpened distal end 128 of a selected needle 124 of a plurality of hollow needles 118 is exposed for medicament delivery. As the needle assembly 102 leaves the first position, the distal end 128 of the selected needle 124 begins to pierce a sealing septum 150 and the remaining plurality of needles 118 are all sealed and sterilized in the sealing septum 150 of the needle assembly 102.

When the housing 110 moves downward, a follower ring 130 and a snap ring 136 move downward as well. As the follower ring 130 moves downward, a follower 132 at a bottom portion of the follower ring 130 engages one of a plurality of external fins 145 of a bottom guide 144. Specifically, the follower 132 contacts one of the plurality of external fins 145 and the follower 132 slides along its tooth shaped edge to rotate the follower ring 130 while maintaining contact with the external fin 145.

A snap ring 136 also rotates because the snap ring 136 is rotationally connected to the follower ring 130. Since the snap ring 136 is rotationally coupled to the follower ring 130, the snap ring 136 applies pressure to an extending portion 142 of a needle post 140 of the selected needle 124. As a result, FIG. 29 illustrates the distal end 128 of the selected needle 124 piercing the sealing septum 150 of the needle assembly 102 and exposing the selected needle 124 for medication delivery.

When the needle assembly 102 is in the second position, as illustrated in FIG. 29, the selected needle 124 amongst the plurality of needles 118 is exposed for medicament delivery. Specifically, the follower 132 has completed rotation and is disposed between external fins 145 of the bottom guide 144. The distal end 128 of the selected needle 124 is ready for medication delivery. In this second position, a proximal end of the selected needle 124 enters into fluid communication with the delivery chamber 274 and the sharpened distal end 128 of the selected needle 124 pierces the sealing septum 150 and is exposed. Each of the plurality of needles 118 is aligned and configured to be in fluid communication with the delivery chamber 274 when selected by the snap ring 136. The proximal end 120 of the remaining needles 118 continues to be disposed in the upper septum 270. The distal end 122 of the remaining needles 118 also continues to stay sealed and sterilized in the sealing septum 150 of the needle assembly 102.

When the needle assembly 102 returns from the second position back to the first position as illustrated in FIG. 28, the user pulls the housing 110 back toward the medication delivery pen 4. At the same time, a cap pushes the snap ring 136 and the follower ring 130 upwards which moves the extending portion 142 of the needle post 140 of the selected needle 124 upward. The distal end 128 of the selected needle 124 returns into the sealing septum 150 of the needle assembly 102. The sealing septum 150 encloses the selected needle 124 and protects the user.

Meanwhile, the follower 132 at the top portion of the follower ring 130 contacts one of a plurality of ridges 117 of a septum housing 114 and causes the follower ring 130 to rotate. The plurality of ridges 117 can be disposed externally or internally to the septum housing 114. The follower 132 at the top portion of the follower ring 130 contacts one of the plurality of external ridges 117 of the septum housing 114 and the follower 132 slides along its tooth shaped edge to rotate the follower ring 130 while maintaining contact with the external ridge 117.

As the needle assembly 102 returns to the first position, as illustrated in FIG. 28, the follower ring 130 rotates and prepares the snap ring 136 to align with an adjacent needle of the plurality of needles 118 for a subsequent injection. Specifically, the snap ring 136 elastically deflects in a radial direction and snaps over the extending portion 142 of the needle post 140 of the adjacent needle of the plurality of needles 118. In this manner, the next needle in the needle assembly 102 is ready for subsequent use.

The process of moving from the first position to the second position and back to the first position while rotating the snap ring 136 repeats in the manner describe above so that each needle amongst the plurality of needles 118 of the needle assembly 102 is individually exposed in a consecutive manner from a first needle, to each adjacent needle and to a last needle.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. An electronic system connectable to a medication delivery pen and a needle assembly, the electronic system exchanging data regarding a medicament traveling from the medication delivery pen to the needle assembly, the electronic system comprising:
 a flow sensor that detects the medicament received from the medication delivery pen to measure flow data of the medicament;
 a circuit board electrically contacting the flow sensor to process and transmit the flow data, the circuit board including a fluid path hole to route a flow of the medicament; and
 a septum body that is configured to provide fluid communication between the flow sensor and one of a plurality of needles of the needle assembly to administer the medicament to a patient; wherein
 the septum body includes an input chamber and a delivery chamber; and
 the input chamber transfers the medicament from the flow sensor to the delivery chamber.

2. The electronic system of claim 1, wherein the fluid path hole provides a medicament flow path between the flow sensor and the septum body.

3. The electronic system of claim 1, wherein the circuit board includes a connector pad that electrically contacts the flow sensor.

4. The electronic system of claim 1, wherein the circuit board includes a short-range wireless communication chip to establish communication with an external source.

5. The electronic system of claim 1, wherein the one of the plurality of needles of the needle assembly pierces the septum body to establish fluid communication between the medication pen and the needle assembly.

6. The electronic system of claim 1, further comprising an activation switch to activate the flow sensor for operation.

7. An electronic system connectable to a medication delivery pen and a needle assembly, the electronic system exchanging data regarding a medicament traveling from the medication delivery pen to the needle assembly, the electronic system comprising:
 a flow sensor that detects the medicament received from the medication delivery pen to measure flow data of the medicament;
 a circuit board electrically contacting the flow sensor to process and transmit the flow data, the circuit board including a fluid path hole to route a flow of the medicament;
 a septum body that is configured to provide fluid communication between the flow sensor and one of a plurality of needles of the needle assembly to administer the medicament to a patient; and
 a hub having a spike that is configured to engage the medication delivery pen and pierce a reservoir septum of the medication delivery pen; wherein
 the flow sensor includes an O-ring that seals an interface between the hub and the flow sensor.

8. The electronic system of claim 7, wherein
 the circuit board includes one or more LEDs to indicate device status; and
 the one or more LEDs is disposed at a proximal end of the circuit board.

9. The electronic system of claim 8, wherein the one or more LEDs of the circuit board surrounds the hub and illuminates the hub to indicate device status.

10. An electronic system connectable to a medication delivery pen and a needle assembly, the electronic system exchanging data regarding a medicament traveling from the medication delivery pen to the needle assembly, the electronic system comprising:
 a flow sensor that detects the medicament received from the medication delivery pen to measure flow data of the medicament;
 a circuit board electrically contacting the flow sensor to process and transmit the flow data, the circuit board including a fluid path hole to route a flow of the medicament;
 a septum body that is configured to provide fluid communication between the flow sensor and one of a plurality of needles of the needle assembly to administer the medicament to a patient; and
 a foam pad surrounding a hub and the flow sensor and applying a force to the circuit board.

11. The electronic system of claim 10, wherein the circuit board surrounds the foam pad.

12. The electronic system of claim 10, further comprising a flexible battery partially surrounding the foam pad.

13. The electronic system of claim 12, wherein the flexible battery partially surrounds the circuit board.

14. The electronic system of claim 12, wherein the flexible battery electrically contacts a distal end of the circuit board.

15. An electronic system connectable to a medication delivery pen and a needle assembly, the electronic system exchanging data regarding a medicament traveling from the medication delivery pen to the needle assembly, the electronic system comprising:
 a flow sensor that detects the medicament received from the medication delivery pen to measure flow data of the medicament;
 a circuit board electrically contacting the flow sensor to process and transmit the flow data, the circuit board including a fluid path hole to route a flow of the medicament; and
 a septum body that is configured to provide fluid communication between the flow sensor and one of a plurality of needles of the needle assembly to administer the medicament to a patient; wherein
 the circuit board comprises a flexible circuit board.

16. An electronic system connectable to a medication delivery pen and a needle assembly, the electronic system exchanging data regarding a medicament traveling from the medication delivery pen to the needle assembly, the electronic system comprising:
 a flow sensor that detects the medicament received from the medication delivery pen to measure flow data of the medicament;
 a circuit board electrically contacting the flow sensor to process and transmit the flow data, the circuit board including a fluid path hole to route a flow of the medicament; and
 a septum body that is configured to provide fluid communication between the flow sensor and one of a plurality of needles of the needle assembly to administer the medicament to a patient;
 wherein the circuit board is disposed between the flow sensor and the septum body.

17. An electronic system connectable to a medication delivery pen and a needle assembly, the electronic system exchanging data regarding a medicament traveling from the medication delivery pen to the needle assembly, the electronic system comprising:
- a flow sensor that detects the medicament received from the medication delivery pen to measure flow data of the medicament;
- a circuit board electrically contacting the flow sensor to process and transmit the flow data, the circuit board including a fluid path hole to route a flow of the medicament;
- a septum body that is configured to provide fluid communication between the flow sensor and one of a plurality of needles of the needle assembly to administer the medicament to a patient;
- a frame including a hole; and
- the circuit board includes a switch, wherein
- the switch is disposed in the hole of the frame and extends through the hole.

18. The electronic system of claim 17, wherein a foam pad applies a force to the switch so that the switch projects through the hole of the frame throughout operation.

19. An electronic system connectable to a medication delivery pen and a needle assembly, the electronic system exchanging data regarding a medicament traveling from the medication delivery pen to the needle assembly, the electronic system comprising:
- a flow sensor that detects the medicament received from the medication delivery pen to measure flow data of the medicament;
- a circuit board electrically contacting the flow sensor to process and transmit the flow data, the circuit board including a fluid path hole to route a flow of the medicament; and
- a septum body that is configured to provide fluid communication between the flow sensor and one of a plurality of needles of the needle assembly to administer the medicament to a patient; wherein
- the septum body includes an upper septum and a lower septum; and
- an inner surface of the lower septum and an outer surface of the upper septum form a delivery chamber.

20. The electronic system of claim 19, wherein the upper septum is disposed within the lower septum.

21. The electronic system of claim 19, wherein the circuit board is rotationally aligned to an input chamber of the septum body.

22. A method of operating an electronic system connectable to a medication delivery pen and a needle assembly, the needle assembly including a plurality of needles, the electronic system exchanging data regarding a medicament traveling from the medication delivery pen to the needle assembly, the method comprising:
- fluidly connecting the medication delivery pen to a flow sensor;
- providing the medicament to flow from the medication delivery pen to the flow sensor to measure flow data of the medicament;
- processing and transmitting the flow data from the flow sensor to a circuit board; and
- routing medicament flow from the flow sensor, through the circuit board and to a septum body of the electronic system for delivery of the medicament to a patient when the septum body is in fluid communication with one of the plurality of needles of the needle assembly; wherein
- the septum body includes an input chamber and a delivery chamber; and
- the input chamber transfers the medicament from the flow sensor to the delivery chamber.

23. An electronic system connectable to a medication delivery pen and a needle assembly, the electronic system exchanging data regarding a medicament traveling from the medication delivery pen to the needle assembly, the electronic system comprising:
- a flow sensor that detects the medicament received from the medication delivery pen to measure flow data of the medicament;
- a circuit board electrically contacting the flow sensor to process and transmit the flow data, the circuit board including a fluid path hole to route a flow of the medicament; and
- a septum body that is configured to provide fluid communication between the flow sensor and one of a plurality of needles of the needle assembly to administer the medicament to a patient wherein
- the fluid path hole provides a medicament flow path between the flow sensor and the septum body; and
- the fluid path hole is offset from a centerline of the electronic system.

* * * * *